United States Patent
Brown et al.

(10) Patent No.: US 12,419,619 B2
(45) Date of Patent: Sep. 23, 2025

(54) ASPIRATION DEVICE

(71) Applicant: YALE UNIVERSITY, New Haven, CT (US)

(72) Inventors: James Elliott Brown, Killingworth, CT (US); Blake Thomson, Franklin, TN (US); Juliana Xavier-Ferrucio, New Haven, CT (US); Diane Krause, Hamden, CT (US); Stephanie Halene, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 717 days.

(21) Appl. No.: 16/344,507

(22) PCT Filed: Oct. 24, 2017

(86) PCT No.: PCT/US2017/058163
§ 371 (c)(1),
(2) Date: Apr. 24, 2019

(87) PCT Pub. No.: WO2018/081181
PCT Pub. Date: May 3, 2018

(65) Prior Publication Data
US 2019/0247027 A1   Aug. 15, 2019

Related U.S. Application Data

(60) Provisional application No. 62/504,090, filed on May 10, 2017, provisional application No. 62/411,780, filed on Oct. 24, 2016.

(51) Int. Cl.
*A61B 10/02* (2006.01)

(52) U.S. Cl.
CPC ........ *A61B 10/025* (2013.01); *A61B 10/0275* (2013.01); *A61B 10/0283* (2013.01); *A61B 2010/0258* (2013.01)

(58) Field of Classification Search
None
See application file for complete search history.

(56) References Cited

U.S. PATENT DOCUMENTS

| 4,810,244 A | 3/1989 | Allen |
| 5,207,648 A | 5/1993 | Gross |

(Continued)

FOREIGN PATENT DOCUMENTS

| GB | 2130890 A | 6/1984 |
| JP | 2010507567 A | 3/2010 |

(Continued)

OTHER PUBLICATIONS

"Some." Merriam-Webster.com Dictionary, Merriam-Webster, https://www.merriam-webster.com/dictionary/some. Accessed Sep. 20, 2023. (Year: 2023).*

(Continued)

*Primary Examiner* — Matthew Kremer
(74) *Attorney, Agent, or Firm* — Riverside Law LLP

(57) ABSTRACT

The present invention provides improved devices for biopsy, aspiration, stem cell acquisition, and methods of using the same. The devices balance aspiration with concurrent infusion to manage changes in pressure at the site of biopsy. The present invention can be adapted for any biopsy, aspiration, or cell harvest procedure, including adipose tissue aspiration and bone marrow aspiration (BMA). In particular, the present invention limits patient pain, prevents blood contamination, and increases cell mobilization, such as improved stem cell yields with intraosseous (IO) pharmacological mobilization of stem cells during a BMA procedure, and with improved stem cell yields using pharmacological mobilization of stem cells from fat. The pharmacological mobilization of cells allows the harvest of cells from a biopsy many fold larger than existing methods.

15 Claims, 28 Drawing Sheets

(56) References Cited

U.S. PATENT DOCUMENTS

| | | | |
|---|---|---|---|
| 5,827,670 A * | 10/1998 | Masinovsky | C07K 16/2836 |
| | | | 435/2 |
| 5,977,034 A * | 11/1999 | Wolfinbarger, Jr. | ............ |
| | | | A61L 2/0088 |
| | | | 510/109 |
| 6,248,110 B1 | 6/2001 | Reiley | |
| 2001/0053888 A1 * | 12/2001 | Athanasiou | A61M 5/20 |
| | | | 604/154 |
| 2003/0032929 A1 | 2/2003 | McGuckin | |
| 2004/0127905 A1 * | 7/2004 | Lim | A61B 17/3468 |
| | | | 604/174 |
| 2004/0191897 A1 * | 9/2004 | Muschler | A61B 17/32002 |
| | | | 435/325 |
| 2005/0173315 A1 | 8/2005 | Bosch | |
| 2007/0003558 A1 * | 1/2007 | von Andrian | A61K 31/00 |
| | | | 424/155.1 |
| 2007/0276352 A1 | 11/2007 | Crocker | |
| 2008/0051825 A1 | 2/2008 | Reiley | |
| 2009/0112119 A1 * | 4/2009 | Kim | A61B 34/35 |
| | | | 600/564 |
| 2009/0297523 A1 * | 12/2009 | Naftolin | A61P 17/00 |
| | | | 435/7.1 |
| 2015/0105690 A1 * | 4/2015 | Hathaway | A61B 10/0283 |
| | | | 600/566 |
| 2015/0374915 A1 * | 12/2015 | Hyde | A61M 5/007 |
| | | | 604/152 |
| 2016/0000415 A1 | 1/2016 | Belsky | |
| 2016/0081732 A1 * | 3/2016 | Baroud | A61B 17/8819 |
| | | | 623/23.62 |
| 2021/0292842 A1 * | 9/2021 | Symmans | A61P 35/04 |

FOREIGN PATENT DOCUMENTS

| | | | | |
|---|---|---|---|---|
| WO | WO-03040304 A2 * | 5/2003 | ......... | A01K 67/0276 |
| WO | 2008019371 A | 2/2008 | | |
| WO | 2015168547 | 11/2015 | | |

OTHER PUBLICATIONS

Bone Marrow Biopsy and Aspirate, UPMC Hillman Cancer Center, https://hillman.upmc.com/patients/community-support/education/miscellaneous/bone-marrow-biopsy-aspirate, Jul. 2011, 2 pages. (Year: 2011).*

Symington, Kenneth et al., Bone marrow procedures move into the 21st century, www.cancernetwork.com/view/bone-marrow-procedures-move-21st-century, Sep. 1, 2010, 7 pages. (Year: 2010).*

Malempati, Suman et al., Bone Marrow Aspiration and Biopsy, N. Engl. J. Med. 2009:361, 3 pages. (Year: 2009).*

Chinese Office Action (including English translation) issued in App. No. CN201780072930X, dated May 27, 2023, 8 pages.

Japanese Office Action (including English translation) issued in JP2019-521757, dated Apr. 25, 2023, 8 pages.

* cited by examiner

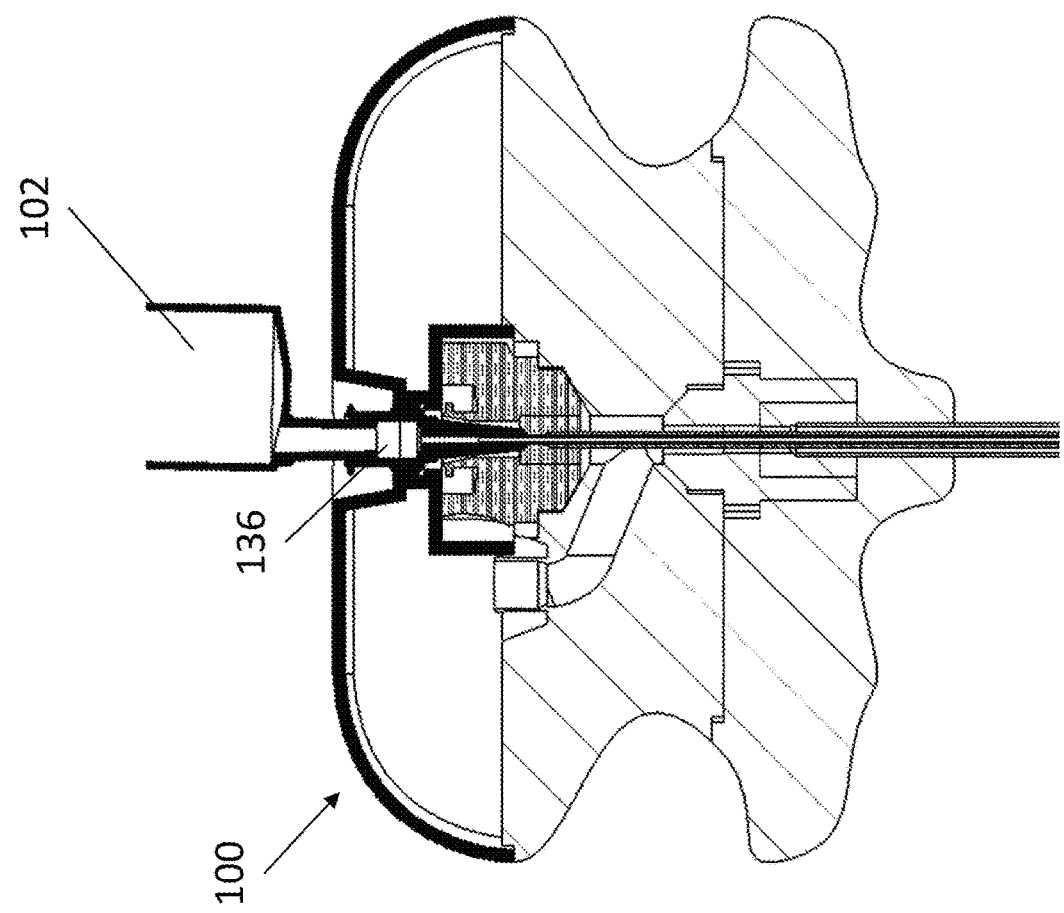
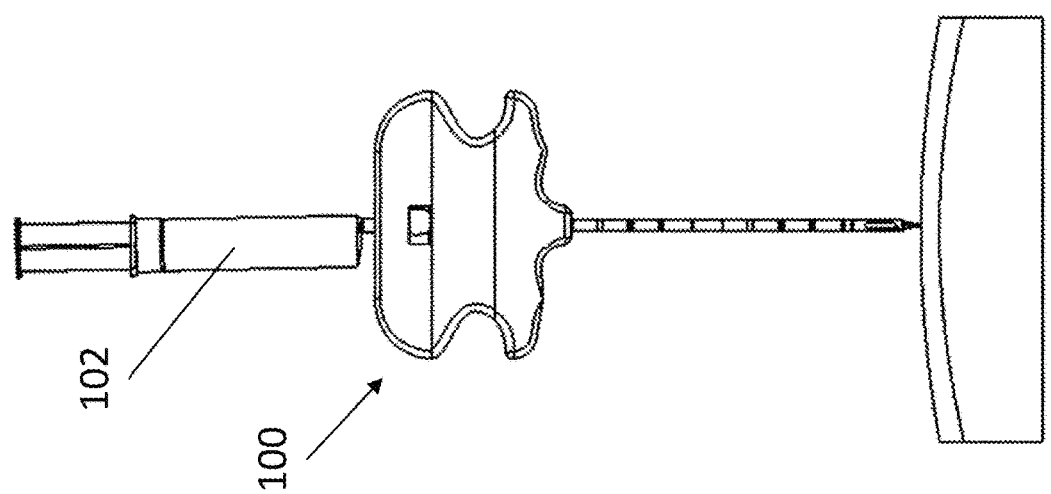
Figure 6

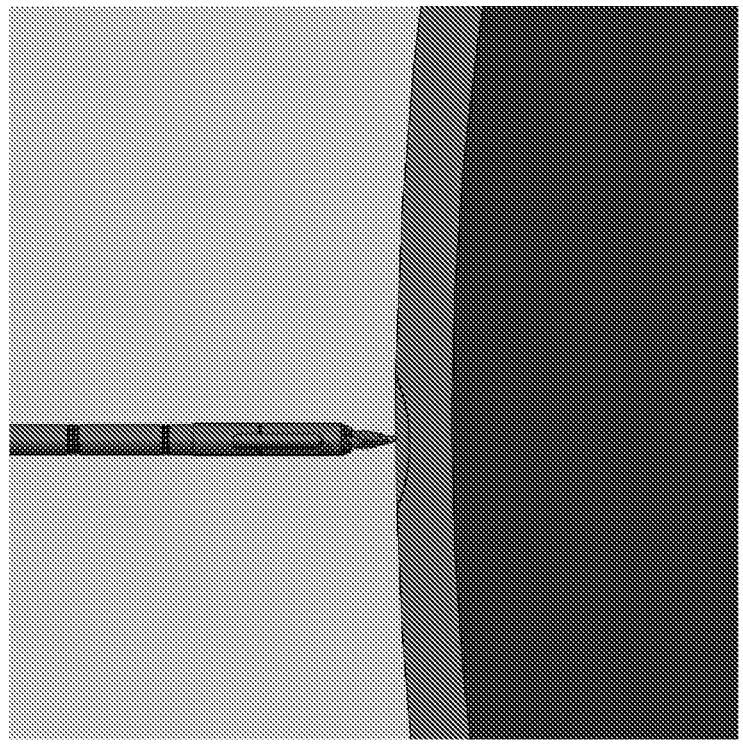
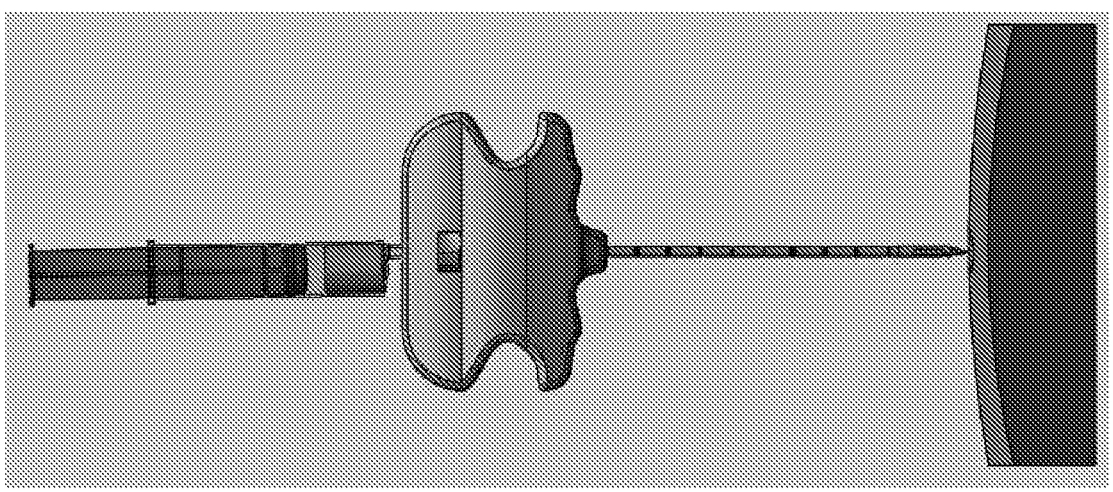

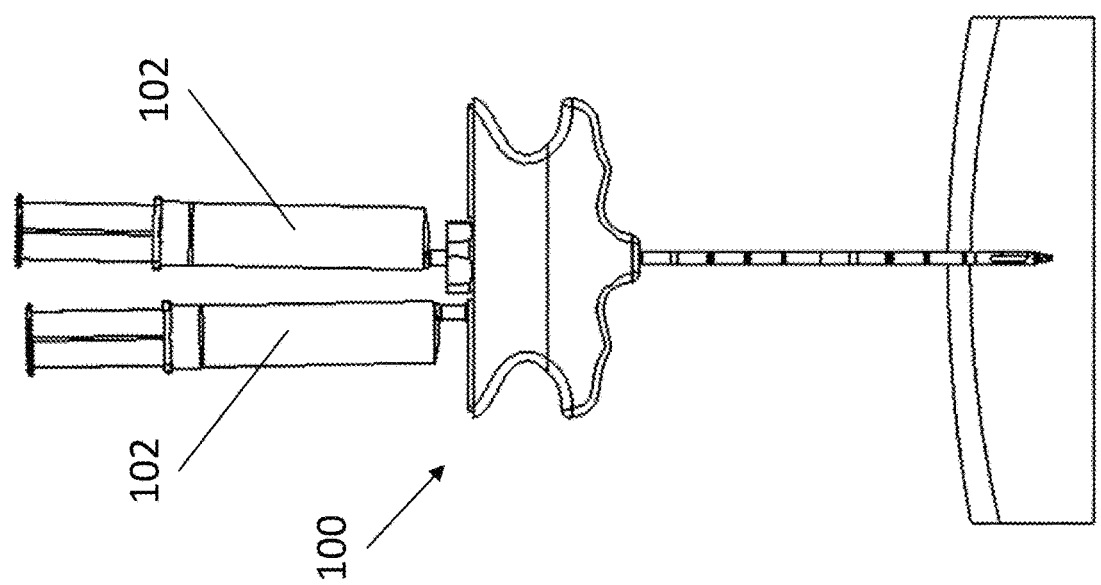

ASPIRATION DEVICE

CROSS-REFERENCE TO RELATED APPLICATIONS

This application is a U.S. national phase application filed under 35 U.S.C. § 371 claiming priority to International Patent Application No. PCT/US17/052163, filed Oct. 24, 2017, which is entitled to priority to U.S. Provisional Application No. 62/411,780, filed Oct. 24, 2016 and U.S. Provisional Application No. 62/504,090, filed May 10, 2017, the contents of each of which are incorporated by reference herein in their entireties.

STATEMENT REGARDING FEDERALLY SPONSORED RESEARCH OR DEVELOPMENT

This invention was made with government support under Grant No. DK106857 from the National Institutes of Health. The government has certain rights in the invention.

BACKGROUND OF THE INVENTION

Stem cells are harvested via numerous routes. Most common among these are acquisition from fat cells and bone marrow. Bone marrow aspirates (BMA) are performed for bone marrow transplantation, blood cancer diagnosis, and regenerative medicine purposes. In the US, about 700,000 BMA procedures are performed annually for blood cancer diagnosis and an estimated 500,000-1,000,000 BMA procedures are performed annually for stem cell therapies and orthopedic procedures. In the field of cancer, BMA is used to diagnose, monitor and study the hematologic malignancies, but poor sampling limits up to 27% of samples in diagnosis. Adequate numbers of cancer cells from BMA are needed for establishing in-vitro colonies and humanized mouse "avatar" models, enabling patient specific in-vivo chemotherapy trials. However, a minimum of $3 \times 10^7$ cancer cells from BMA are required for xenotransplantation and only half of BMA reach this threshold in some diseases (Rongvaux A et al., Nature biotechnology 32.4 (2014): 364-372).

Different types of stem cells can be harvested from bone marrow—the hematopoietic stem cells (HSC), the epithelial stem cells (ESC), and the mesenchymal stem cell (MSC). The regenerative medicine field is rapidly advancing with hundreds of clinical trials registered with the FDA at the time of this writing. The field is expected to provide patients with 3D printed organs and joint surfaces, bone regeneration (Zigdon-Giladi H et al., World journal of stem cells 7.3 (2015): 630), intervertebral disc regeneration (Vadalá G et al., World journal of stem cells 8.5 (2016): 185; Vadalá G et al., Journal of biological regulators and homeostatic agents 30.4 Suppl 1 (2016): 173) among a myriad of other novel orthopedic applications (Lodi D et al., Journal of Experimental & Clinical Cancer Research 30.1 (2011): 9; Cavallo C et al., Journal of biological regulators and homeostatic agents 30.2 (2016): 409; Chahla J et al., Orthopaedic journal of sports medicine 4.1 (2016): 1-8; Cruz-Pardos A et al., Hip international: the journal of clinical and experimental research on hip pathology and therapy 26 (2016): 432-7; Gianakos A et al., Journal of orthopaedic trauma 30.1 (2016): 1-9; Hernigou P et al., International Orthopaedics 41.1 (2017): 127-132; Holton J et al., Orthopedic reviews 8.3 (2016): 6659; Khafagy W W et al., Colorectal Disease 19.1 (2017):066-074; Kim S J et al., Cell Transplantation (2017); Lanham N S et al., Foot & Ankle Specialist (2016): 1938640016679697; Prologo J D et al., Clinical radiology 71 (2016): 307-11). Stem cells "hone in" to sites of injury/degeneration and, due to their anti-inflammatory nature, may treat autoimmune diseases (Ullah I et al., Bioscience reports 35.2 (2015): e00191). There are several ongoing clinical trials for autoimmune diseases regarding the use of stem cells (Ullah I et al., Bioscience reports 35.2 (2015): e00191). For example, one use includes spinal fusion, where stem cells aspirated from bone marrow are added to synthetic bone graft to rapidly form new bone fusing vertebral bodies together (Clough B H et al., The Spine Journal 17.3 (2017): 418-430).

Common problems in current BMA procedures include low counts of the desired cell type, hemodilution, and pain. Bone is a large venous space, with the venous blood bathing the parenchyma-attached stem cells continuously. The vacuum created by syringe suction creates a pressure gradient from syringe to bone to peripheral blood. Blood, being less viscous, flows preferentially to marrow (Gurkan U A et al., Annals of biomedical engineering 36.12 (2008): 1978-1991). Multiple studies have demonstrated that only 1-2 mL of marrow can reliably be obtained from a single position, and the larger the volume aspirated from a single position, the lower the yield (Batinić D et al., Bone marrow transplantation 6.2 (1990): 103-107; Muschler G F et al., J Bone Joint Surg Am 79.11 (1997): 1699-1709; Bacigalupo A et al., Bone marrow transplantation 9.6 (1992): 467-470; Helgestad J et al., Pediatric blood & cancer 57.2 (2011): 224-226; Li J et al., Chinese Journal of Cancer Research 23.1 (2011): 43-48; Wang T F et al., Biology of Blood and Marrow Transplantation 17.3 (2011): 351-355; Loken M R et al., Cytometry Part B: Clinical Cytometry 76.1 (2009): 27-36; Fennema E M et al., Acta orthopaedica 80.5 (2009): 618-621; Riley R S et al., Journal of clinical laboratory analysis 18.2 (2004): 70-90). Other experiments with radio-labeled red cells suggest that stem cells are aspirated within the blood fluid volume (Holdrinet R S G et al., Experimental hematology 8 (1980): 103-7). In summary, bone marrow aspirations as currently performed yield only low numbers of mesenchymal stem cells, about 1-10 cells per $1 \times 10^5$ cells or 0.0001%-0.01% of all bone marrow nucleated cells.

Hemodilution in the cancer field, even for the low volumes of a typical cancer evaluation (7 ml), create an aspicular, hemodilute sample which limits diagnosis. A recent study at a tertiary care institution quantified the proportion of aspirates not compensated for by advanced pathologic and histologic techniques in a retrospective review of bone marrow aspiration and biopsies (BMAB). 350 patients had at least one bad aspirate and at least 1 subsequent aspirate for comparison. Of 1250 aspirates in those 350 patients, 470 (27%) were limited and 58% of these were felt to be clinically significant in that they were not compensated for by the core, flow cytometry, or cytogenetics. 7.7% required a re-biopsy and 4% had a missed major diagnosis. An additional retrospective review of the donation registry of patients with myelodysplastic syndromes (MDS) was performed and the cell count was compared by disease subtype classification. A rough cut-off of $3 \times 10^7$ cells are required for xenotransplantation. Only 52% of these procedures yielded sufficient cells for transplantation.

Hemodilution in the orthobiologics field impacts the success of procedures, as they significantly depend on the number of stem cells that are obtained during BMA. Each patient has a different stem cell profile, with older and sickly patients generally having less stem cells available in bone marrow and other tissue. Up to 60 mL is often taken from a single site, amounting to an enormous amount of peripheral blood. Because of the difficulties that arise from harvesting cells from bone marrow, there is interest in obtaining stem cells from fat. Adipose tissue is an attractive source of MSCs for stem cell therapy because it is easily obtainable in sufficient quantities by a minimally invasive procedure. Furthermore, adipose tissue contains more MSCs than does the bone marrow (about 100,000 MSCs per gram of fat). However, the sampling method is still limited as to the amount of fat that can be aspirated directly with the device.

BMA is a source of moderate to severe pain in up to 87% of patients (Vanhelleputte P et al., Journal of pain and symptom management 26.3 (2003): 860-866; Mainwaring C J et al., International Journal of Laboratory Hematology 18.4 (1996): 285-288; Vigneault L et al., Canadian Journal of Anesthesia 58.1 (2011): 22-37). Pain is a deterrent in blood cancer trials and a limiting factor for bone marrow donation by healthy individuals as it is an important cause for bone marrow registry attrition (Switzer G E et al., Bone marrow transplantation 24.3 (1999); Johansen K A et al., Transfusion Medicine 18.4 (2008): 250-259; Hyde M K et al., Psychology, health & medicine 19.1 (2014): 115-125). It also increases the costs to hospitals to provide procedural sedation to treat the pain.

Therefore, there is a need in the art to increase the yield of stem cells from both fat and bone marrow and to decrease the pain of bone marrow aspiration. The present invention addresses this need.

SUMMARY OF THE INVENTION

In one aspect, the present invention relates to an aspiration device comprising: at least one first elongate member having a lumen extending between a proximal opening and a distal tip opening; and a second elongate member having a lumen extending between a proximal opening and a distal tip opening, and at least one lateral opening to the lumen along a length of the second elongate member; wherein the at least one first elongate member is positioned within the lumen of the second elongate member such that the distal tip of the at least one first elongate member extends through the distal tip opening of the second elongate member; and wherein the distal tip of the at least one first member forms a sealing engagement with the second elongate member between the distal tip opening and the at least one lateral opening of the second elongate member.

In one embodiment, the at least one first elongate member is sized such that while positioned within the lumen of the second elongate member, a flow path remains from the at least one lateral opening to the proximal opening of the second elongate member.

In one embodiment, the device further comprises a third elongate member having a lumen extending between a proximal opening and a distal tip opening, the third elongate member being sized to fit within the lumen of the at least one first elongate member.

In one embodiment, the sealing engagement is formed by a gasket, a spacer, or a screw thread. In one embodiment, the distal tip opening of the at least one first elongate member is positioned at a distance of between about 1 mm and 1000 mm from the at least one lateral opening of the second elongate member. In one embodiment, each of the at least one lateral opening extends along the second elongate member for a length of between 5 and 25 mm.

In one embodiment, the at least one first elongate member is a plurality sharing a single proximal opening. In one embodiment, the at least one first elongate member is a plurality sharing a single distal tip opening. In one embodiment, the proximal opening of the at least one first elongate member and the proximal opening of the at least one second elongate member are each fluidly connectable to a solution reservoir. In one embodiment, the solution reservoir comprises a composition selected from a cell mobilizing composition, a pain reducing composition, and combinations thereof.

In one embodiment, the cell mobilizing composition comprises a modulator of a molecule within the molecular pathway involved with cell adhesion or cell mobilization selected from the group consisting of: a modulator of the integrin family such as the VLA-4 molecule inhibitors firategast, UNII-OJY3SK9H5F, and BIO5192, a modulator of CXCL12/CXCR4 interaction such as AMD3100, a modulator of CXCR7 molecule, CXCL12 analogues, a modulator of nerve/stem cell interaction such as via dopamine modulation or by inhibiting nerve axon firing, a modulator of an adhesion molecule, integrins, G-protein coupled receptors, SIP-1 agonists, endocrine targets, plerixafor, granulocyte colony-stimulating factor (G-CSF), PEGylated and glycosylated versions of G-CSF, granulocyte macrophage colony-stimulating factor (GM-CSF), macrophage colony stimulating factor (M-CSF), tyrosine kinase 3 (FLT-3), ancestim, stem cell factor, a cytokine (including interleukin-1, interleukin-3, interleukin-6, interleukin-7, interleukin-11, and interleukin-12), a metalloproteinase, a serine protease, a cysteine protease, a peptidase, a chemokine, multiple chemotherapies such as cyclophosphamide, and combinations thereof.

In one embodiment, the pain reducing composition is selected from the group consisting of: lidocaine, prilocaine, tetracaine, benzocaine, procaine, mepivacaine, bupivacaine, etidocaine, tropacocaine, piperocaine, stovaine, cyclomethycaine, parethoxycaine, dyclonine, falicain, pramoxine, amolanone, phenacene, deprodone, dibucaine, and combinations thereof.

In another aspect, the present invention relates to a method of tissue aspiration, comprising the steps of: providing an aspiration device having at least one first elongate member with a lumen extending between a proximal opening and a distal opening and at least one second elongate member having a lumen extending between a proximal opening and a distal opening; inserting the aspiration device into a tissue such that the distal opening of the at least one first elongate member and the distal opening of the at least one second elongate member are positioned near a biopsy site; administering at least one solution through the at least one first elongate member to a first region of the biopsy site; and extracting at least one aspirate through the at least one second elongate member from a second region adjacent to the first region of the biopsy site.

In one embodiment, the inserting step is supplemented by administering at least one pain reducing solution through the lumen of the at least one first elongate member. In one embodiment, the tissue is bone marrow tissue. In one embodiment, the tissue is adipose tissue.

In one embodiment, the at least one solution includes a pain reducer selected from the group consisting of: lidocaine, prilocaine, tetracaine, benzocaine, procaine, mepivacaine, bupivacaine, etidocaine, tropacocaine, piperocaine, stovaine, cyclomethycaine, parethoxycaine, dyclonine, falicain, pramoxine, amolanone, phenacene, deprodone, dibucaine and combinations thereof.

In one embodiment, the at least one solution includes a cell mobilizing composition comprising a modulator of a molecule within the molecular pathway involved with cell adhesion or cell mobilization selected from the group consisting of: a modulator of the integrin family such as the VLA-4 molecule inhibitors firategast, UNII-OJY3SK9H5F, and BIO5192, a modulator of CXCL12/CXCR4 interaction such as AMD3100, a modulator of CXCR7 molecule, CXCL12 analogues, a modulator of nerve/stem cell interaction such as via dopamine modulation or by inhibiting nerve axon firing, a modulator of an adhesion molecule, integrins, G-protein coupled receptors, S1P-1 agonists, endocrine targets, plerixafor, granulocyte colony-stimulating factor (G-CSF), PEGylated and glycosylated versions of G-CSF, granulocyte macrophage colony-stimulating factor (GM-CSF), macrophage colony stimulating factor (M-CSF), tyrosine kinase 3 (FLT-3), ancestim, stem cell factor, a cytokine (including interleukin-1, interleukin-3, interleukin-6, interleukin-7, interleukin-11, and interleukin-12), a metalloproteinase, a serine protease, a cysteine protease, a peptidase, a chemokine, multiple chemotherapies such as cyclophosphamide, and combinations thereof.

In one embodiment, the first region and the second region are separated by a distance between 1 mm and 1000 mm. In one embodiment, the administering step and the extracting step are performed concurrently. In one embodiment, the administering step comprises a sequential administration of a CXCR4 inhibitor, a VLA-4 or metalloproteinase or ISP-1 agonist, a compound that modulates neural-stem cell control, and a molecule that impairs cell adhesion. In one embodiment, the administering step is performed first, and the extracting step is performed after a delay of between 30 seconds and 120 minutes.

In one embodiment, the aspirate comprises one or more cells selected from the group consisting of: hematopoietic stem cells, mesenchymal stem cells, epithelial stem cells, stromal cells, gland cells, nerve cells, fat cells, germ cells, and combinations thereof. In one embodiment, less than 10% of the one or more cells are blood cells.

In one embodiment, the mean pressure change in the first region and the second region is between 15 to 50 mmHg.

In one embodiment, the method further comprises the step of: collecting a tissue sample within the lumen of at least one of the first or second elongate member.

In another aspect, the present invention relates to a method of tissue aspiration, comprising the steps of: providing an aspiration device having at least one elongate member with a lumen extending between a proximal opening and a distal opening; inserting the aspiration device into a tissue such that the distal opening of the at least one elongate member is positioned near a biopsy site; administering at least one cell mobilizing composition through the at least one elongate member into the biopsy site; and extracting at least one aspirate through the at least one elongate member.

In one embodiment, the inserting step is supplemented by administering at least one pain reducing solution through the at least one elongate member. In one embodiment, the tissue is bone marrow tissue. In one embodiment, the tissue is adipose tissue.

In one embodiment, the at least one cell mobilizing composition comprises a modulator of a molecule within the molecular pathway involved with cell adhesion or cell mobilization selected from the group consisting of: a modulator of the integrin family such as the VLA-4 molecule inhibitors firategast, UNII-OJY3SK9H5F, and BIO5192, a modulator of CXCL12/CXCR4 interaction such as AMD3100, a modulator of CXCR7 molecule, CXCL12 analogues, a modulator of nerve/stem cell interaction such as via dopamine modulation or by inhibiting nerve axon firing, a modulator of an adhesion molecule, integrins, G-protein coupled receptors, S1P-1 agonists, endocrine targets, plerixafor, granulocyte colony-stimulating factor (G-CSF), PEGylated and glycosylated versions of G-CSF, granulocyte macrophage colony-stimulating factor (GM-CSF), macrophage colony stimulating factor (M-CSF), tyrosine kinase 3 (FLT-3), ancestim, stem cell factor, a cytokine (including interleukin-1, interleukin-3, interleukin-6, interleukin-7, interleukin-11, and interleukin-12), a metalloproteinase, a serine protease, a cysteine protease, a peptidase, a chemokine, multiple chemotherapies such as cyclophosphamide, and combinations thereof.

In one embodiment, the at least one cell mobilizing composition further includes a pain reducer selected from the group consisting of: lidocaine, prilocaine, tetracaine, benzocaine, procaine, mepivacaine, bupivacaine, etidocaine, tropacocaine, piperocaine, stovaine, cyclomethycaine, parethoxycaine, dyclonine, falicain, pramoxine, amolanone, phenacene, deprodone, dibucaine and combinations thereof.

In one embodiment, the administering step comprises a sequential administration of a CXCR4 inhibitor, a VLA-4 or metalloproteinase or ISP-1 agonist, a compound that modulates neural-stem cell control, and a molecule that impairs cell adhesion. In one embodiment, the administering step is performed first, and the extracting step is performed after a delay of between 30 seconds and 120 minutes.

In one embodiment, the aspirate comprises one or more cells selected from the group consisting of: hematopoietic stem cells, mesenchymal stem cells, epithelial stem cells, stromal cells, gland cells, nerve cells, fat cells, germ cells, and combinations thereof. In one embodiment, less than 10% of the one or more cells are blood cells.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 6 depicts a syringe mated to the handle portion of an exemplary aspiration device, such as in a drilling configuration.

FIG. 7A and FIG. 7B depict an infusion step during drilling using an exemplary aspiration device. In FIG. 7A, the aspiration device is shown positioned near an aspiration site and a mated syringe is prepared with an infusion solution. In FIG. 7B, the infusion of solution occurs at the distal tip of the aspiration device.

In FIG. 10A, the aspiration device is shown inserted into bone marrow and a mated syringe is prepared for aspiration. In FIG. 10B, directional aspiration is achieved using a single lateral opening.

FIG. 11 depicts two syringes mated to the handle portion of an exemplary aspiration device, such as in a concurrent aspiration and infusion configuration.

FIG. 12A shows the cannula portion removing a biopsy core. FIG. 12B is a magnified view illustrating the retention of the biopsy core via the internally threaded tip.

FIG. 15A depicts a trocar. FIG. 15B depicts a drill bit.

FIG. 27A depicts the colony forming unit (CFU) per mL of aspirate, calculated to account for differences in cell number of an aspirate. Stem cells form colonies by duplication and differentiation whereas non-stem cells do not. Therefore the number of colonies is an accepted measure of stem cell acquisition. When controlled for number of cells, the pressure release mechanism and the pharmacologic mobilizer mechanism both had much higher number of colonies per white cell than the control, consistent with decreased blood contamination. Note that when the stem cell mobilization drugs were given via the control device and aspiration performed through the same channel as the drug administration, the number of cells is significantly lower than even the control, showing the importance of the device in the mechanism for drug delivery and harvest. FIG. 27B depicts the results of FIG. 27A normalized for cell number. When total colonies are counted rather than controlling for number of white cells, the importance of the pressure release mechanism and the drug mobilization methods are apparent because the methods obtain much higher total white count yields, demonstrating that using device methods alone and in combination with pharmacologic mobilization methods, the stem cell yield is significantly higher.

DETAILED DESCRIPTION

Figure 1:
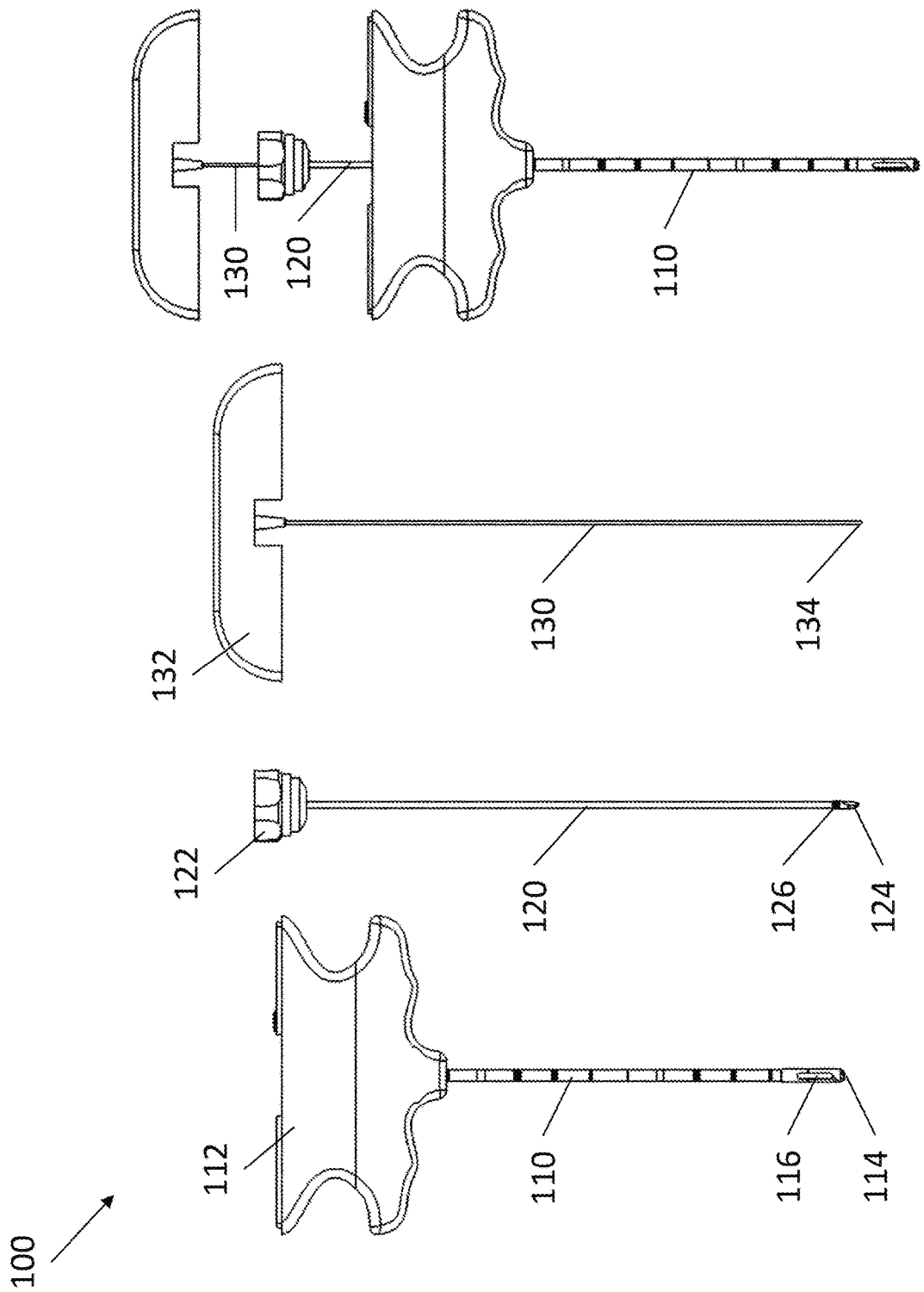
FIG. 1 depicts the individual components of an exemplary aspiration device comprising a cannula, a trocar, and a stylet.

The present invention provides improved devices for biopsy, aspiration, stem cell acquisition, and methods of using the same. The devices balance aspiration with concurrent infusion to manage changes in pressure at the site of biopsy. The present invention can be adapted for any biopsy, aspiration, or cell harvest procedure, including adipose tissue aspiration and bone marrow aspiration (BMA). In particular, the present invention limits patient pain, prevents blood contamination, and increases cell mobilization, such as improved stem cell yields with intraosseous (IO) pharmacological mobilization of stem cells during a BMA procedure, and with improved stem cell yields using pharmacological mobilization of stem cells from fat. The pharmacological mobilization of cells allows the harvest of cells from a biopsy many fold larger than existing methods.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"Anesthetic" as used herein refers to an agent that produces a reversible loss of sensation in an area of a subject's body. An example of an anesthetic is lidocaine.

"Aspicular sample" as used herein refers to a liquid sample of bone marrow which does not contain "spicules." Spicules are particles of bone parenchyma that contain the stem cells used for analysis; without a spicule evaluation is quite limited and stem cell yields are poor.

"Bone access needle" as used herein refers to a device used to access the bone marrow cavity space through the hard cortex of a bone.

"Distal" as used herein refers to the bottom end of a device remote from point of attachment or origin. In disclosed embodiment, distal refers to the end furthest away from a medical professional when introducing a device in a patient. "Proximal" as used herein refers to the closest end of a device situated nearer to the center of the body or the point of attachment. In disclosed embodiments, proximal refers to the end closest to a medical professional when placing a device in the patient.

"Dry tap" as used herein refers to the instance where no liquid marrow can be obtained during a bone marrow aspiration. This occurs in needle malplacement, or in situations where the venous blood normally within the bone is replaced by fibrous tissue or tumor cells.

"Intraosseous infusion" as used herein refers to the process of injecting a therapeutic agent directly into the marrow of a bone.

"Intramedullary space" as used herein refers to the space within the marrow cavity of a bone.

"Lumen" as used herein refers to a canal, duct or cavity within a tubular structure.

"Axially integrated" as used herein refers to a condition of being integrated along the longitudinal axis of a structure.

"Channel" as used herein refers to a conduit, duct or any type of longitudinal hollow path-way used for transport in either longitudinal direction. For example a channel may be used for the delivery of an anesthetic agent down the channel from a syringe to target anatomical site or a channel may be used for the transport of tissue or cell samples up the channel from an anatomical site or a lesion into a syringe.

"Infusion" as used herein refers to a process of slow introduction of an element, for example a solution, into or onto a target.

"Internal anatomical space" as used herein refers to any region and/or site that exist below external skin layer. An internal anatomical space may comprise a cavity and/or a cellular structure.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween. This applies regardless of the breadth of the range.

Aspiration Device

The present invention includes aspiration devices that can be adapted for bone marrow aspiration in cancer diagnosis, bone marrow harvesting, stem cell harvesting for regenerative medicine or scientific purposes, intraosseous infusion, trabecular bone harvesting, bone biopsy, and the like. Under the umbrella of regenerative medicine, the devices of the present invention can also be used for orthopedic and spinal fusion devices. The devices of the present invention can be used separately or integrated within orthopedic or spinal fusion systems. For example, the device can be incorporated into a system that places pedicle screws to obtain marrow from the vertebrae at the time of spinal fusion. The devices reduce patient pain, consolidate procedural steps, increase sample yields of marrow and stem cells, exclude peripheral blood (hemodilution), and eliminate aspiration artifact during core biopsies. The devices modulate the pressure in the bone during these procedures to increase yield and reduce pain, which may be an active mechanism (injection into bone) or passive (the negative pressure/suction from a device such as a syringe to harvest the bone marrow draws in fluid through a second channel to reduce or decompress the negative pressure from the suction). The unique design also allows the harvesting of bone particles in the setting of a "dry tap" for cancer analysis. The design of the large side hole is able to decrease the "aspicular sample" rate.

Referring now to FIG. 1, an exemplary aspiration device 100 is depicted. Device 100 comprises cannula 110, trocar 120, and stylet 130. In some embodiments, stylet 130 may fit within trocar 120, and trocar 120 may fit within cannula 110, such that stylet 130, trocar 120, or cannula 110 may be concentric. In other embodiments, stylet 130, trocar 120, and cannula 110 may be positioned adjacent to one another. For example, in some embodiments, stylet 130, trocar 120, or cannula 110 may be bonded or welded side-by-side. Device 100 can also comprise one or more brackets or slip fittings to releasably hold stylet 130, trocar 120, or cannula 110 adjacent to one another. In other embodiments, stylet 130, trocar 120, or cannula 110 may be used independently as separate components.

Cannula 110 is an elongate hollow tube having a cannula lumen 119 running throughout. Cannula 110 comprises proximal handle 112, distal open end 114, and at least one lateral opening 116 near distal open end 114. Lateral opening 116 can be positioned any suitable distance from distal open end 114, such as between 1 mm and 1000 mm. A large single lateral opening 116 allows rotational control of where the aspiration takes place, allowing for a much larger sampling area from a single hole, up to 48 times or greater than a traditional end-hole device. In some embodiments lateral opening 116 has an elongated shape to increase the chance it will cross an island of hematopoietic marrow containing stem cells, rather than fatty marrow which contains only fat. Lateral opening 116 can have any suitable length, such as between 5 and 25 mm. In some embodiments, cannula 110 comprises two, three, four, five, or more lateral openings. Distal open end 114 can comprise one or more cutting teeth or flutes. Cannula 110 can have any suitable dimensions. For example, cannula 110 can have a length and a tube size comparable to bone marrow aspiration needles commonly used in the art, such as a length between 2 and 10 inches and a tube size between 8 and 19 Gauge. In some embodiments, cannula 110 can comprise spaced markings along its exterior to indicate depth of insertion.

Trocar 120 is an elongate hollow tube having a lumen 129 running throughout. Trocar 120 comprises proximal grip 122, distal tapered end 124, and a threaded region 126 positioned near distal tapered end 124. Trocar 120 is sized to fit within cannula lumen 119. Preferably, the outer diameter of trocar 120 is smaller than the inner diameter of cannula lumen 119 to permit the passage of fluids for purposes that will be explained elsewhere herein. Threaded region 126 can be engaged to a threaded region near the distal end of cannula lumen 119, as shown in FIG. 4.

Stylet 130 is an elongate hollow tube having a stylet lumen 138 running throughout. Stylet 130 comprises proximal handle 132, and distal open end 134. Stylet 130 is sized to fit within lumen 129 of trocar 120. In certain embodiments, stylet 130 fits flush within lumen 129 of trocar 120, such that there is minimal space between stylet 130 and trocar 120.

Figure 2:
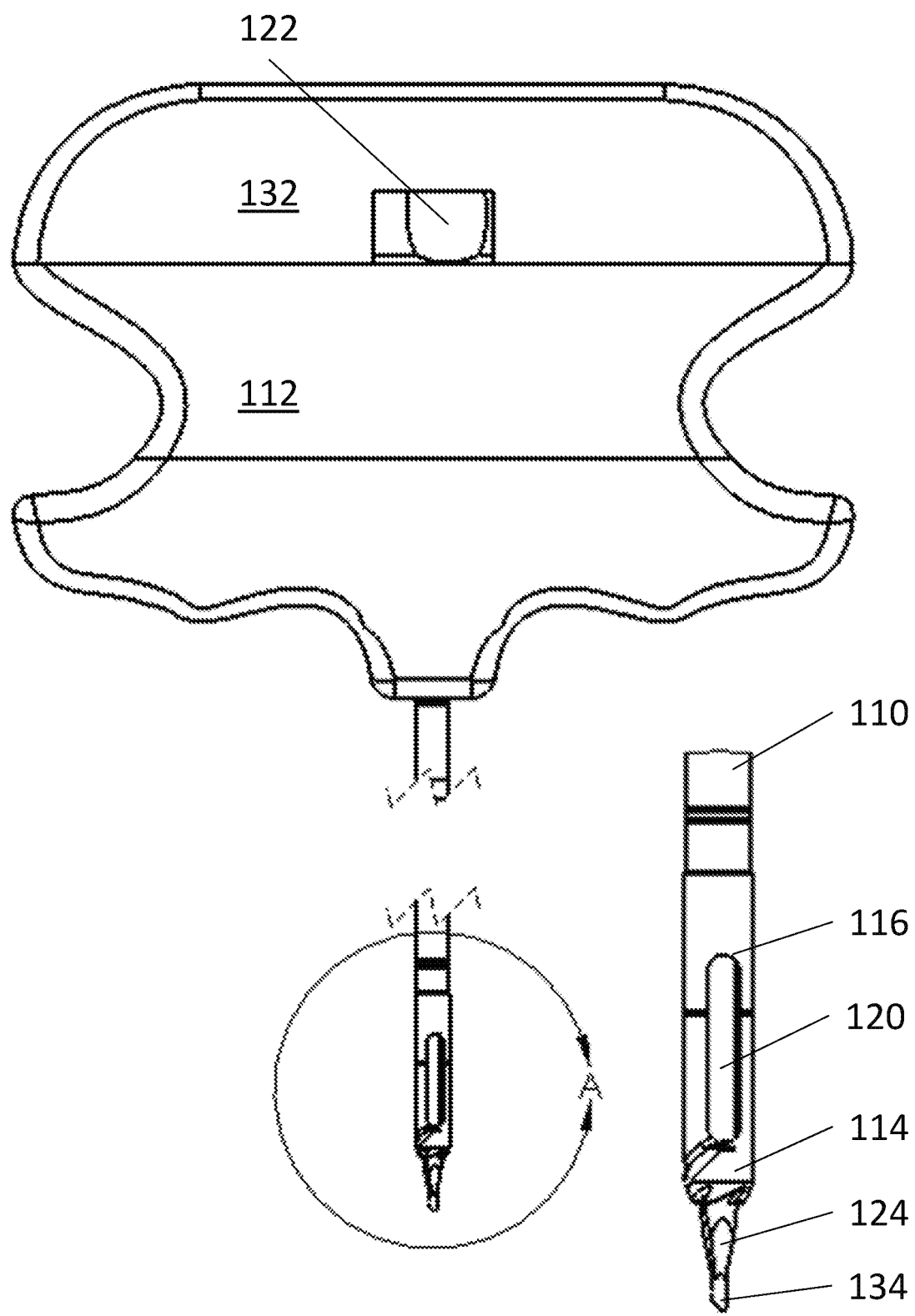
FIG. 2 depicts an exemplary aspiration device in a configuration that is drivable into a target aspiration site.
Figure 3:
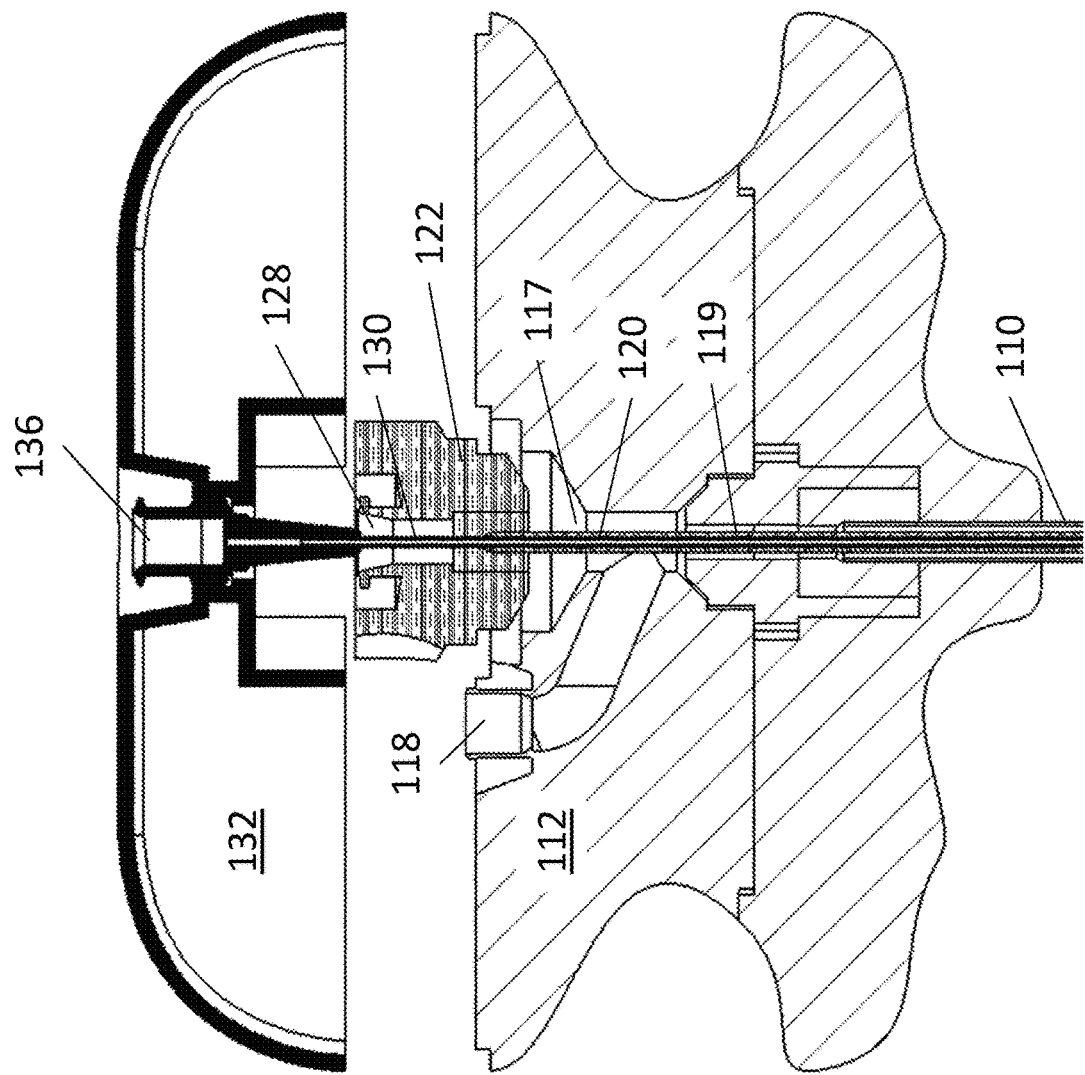
FIG. 3 depicts a cross-sectional view of the handle portion of an exemplary aspiration device.
Figure 4:
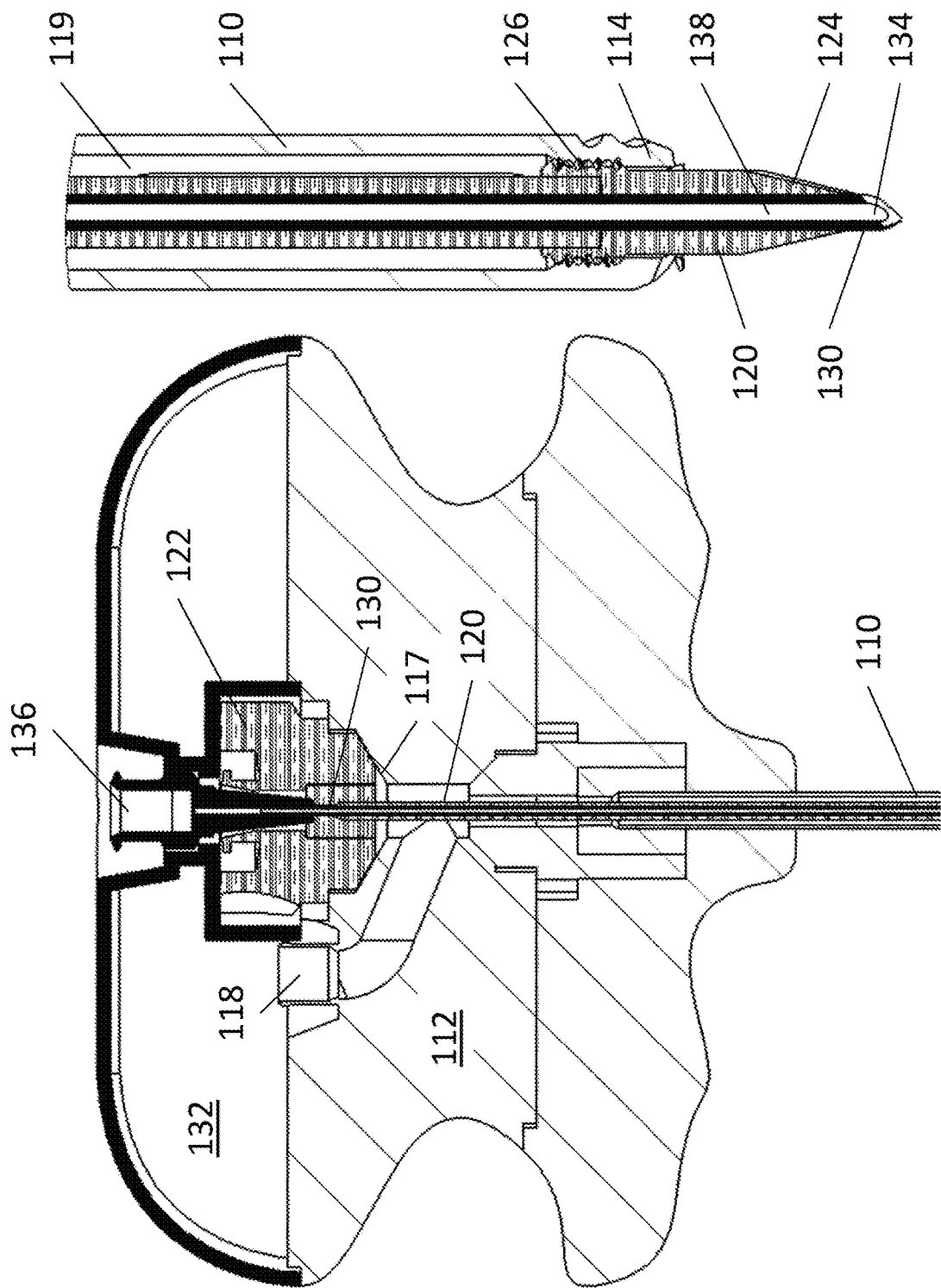
FIG. 4 depicts cross-sectional views of the handle portion (left) and distal end (right) of an exemplary aspiration device.

Referring now to FIG. 2, FIG. 3, and FIG. 4, the proximal and distal structures of an assembled device 100 is depicted. Proximal handle 112, proximal grip 122, and proximal handle 132 fit together to form a single larger handle. Distal tapered end 124 of trocar 120 can be positioned to extend past distal open end 114 of cannula 110. Distal open end 134 of stylet 130 can be positioned to extend past distal tapered end 124 of trocar 120. The combined distal ends thereby form a piercing point suitable for drilling into bone.

FIG. 3 depicts a cross-sectional exploded view of the proximal handle 112, proximal grip 122, and proximal handle 132. This represents a tri-axial assembly in which there is a proximal open end 136 (connecting to its counterpart distal open end 134 by stylet lumen 138) accepting a needle nested in proximal open end 128 (connecting to its counterpart distal tapered end 124 by trocar lumen 129), which is central to the cannula 110. The cross-sectional view reveals proximal open end 128 in trocar 120 and proximal open end 136 in stylet 130. The cross-sectional view also reveals proximal side lumen 118 extending laterally from proximal open end 117 in cannula 110. Proximal side lumen 118 provides a means of accessing cannula lumen 119.

In FIG. 4, a cross-sectional view of the proximal and distal structures of an assembled device 100 is shown. Of note, in the assembled proximal structures, proximal grip 122 forms an airtight seal with proximal open end 117, such that cannula lumen 119 fluidly extends from its distal end through proximal side lumen 118. In the assembled distal structures, the threaded engagement in threaded region 126 between cannula 110 and trocar 120 is visible. A gap is also evident between the inner diameter of cannula lumen 119 and the outer diameter of trocar 120, with the gap allowing the transfer of fluid through the at least one lateral opening 116.

While proximal side lumen 118 is depicted in FIG. 4 as being embedded in proximal handle 112 and blocked by handle 132, persons having skill in the art will understand that any implementation of proximal side lumen 118 is contemplated. For example, proximal side lumen 118 may be extendable through proximal handle 132 and accessible by an additional opening on proximal handle 132.

In some embodiments, the proximal means of accessing the lumens of device 100 are positioned such that the proximal handles of device 100 can be manipulated or rotated independently from the lumens. In a first example, in some embodiments proximal side lumen 118 may extend from cannula 110 from the side or below proximal handle 112 as a separately rotatable structure, such that proximal handle 112, proximal grip 122, and proximal handle 132 may be rotated independently from proximal side lumen 118 (not pictured).

Figure 5:
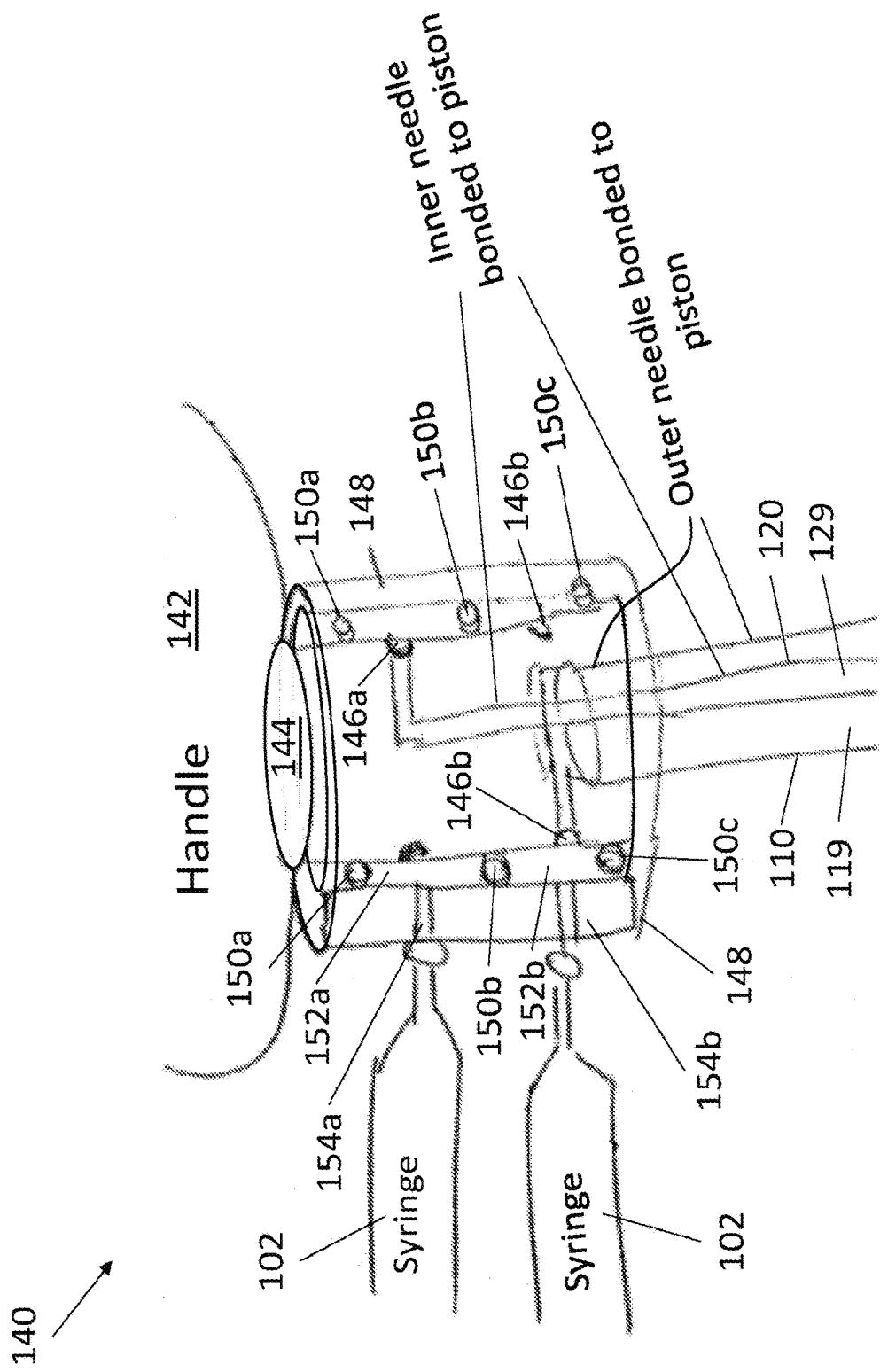
FIG. 5 depicts a diagram of an exemplary aspiration device having lumens that are rotatable independently from their access ports while maintaining their fluid connections.

In a second example depicted in FIG. 5, aspiration device 140 provides access points to both cannula lumen 119 and trocar lumen 129 that are independently rotatable from cannula lumen 119 and trocar lumen 129. Aspiration device comprises a proximal handle 142 connected to a fluid transfer drum 144. Fluid transfer drum 144 has a substantially cylindrical shape with a diameter and a vertically aligned longitudinal axis, the cylindrical shape having a proximal portion and a distal portion. Fluid transfer drum 144 comprises a centrally located pocket in its distal end, the pocket extending into the distal end of fluid transfer drum 144 for a depth. Fluid transfer drum 144 comprises at least one channel opening 146a positioned on the surface of the proximal portion and at least one channel opening 146b positioned on the surface of the distal portion.

The at least one channel opening 146a opens into a centrally located channel aligned with the longitudinal axis of fluid transfer drum 144, the centrally located channel terminating in an opening positioned at the top of the pocket in the distal end of fluid transfer drum 144. The opening positioned at the top of the pocket in the distal end of fluid transfer drum 144 is connectable to trocar 120, such that a fluid connection is made between the at least one channel opening 146a, the centrally located channel, and trocar lumen 129.

The at least one channel opening 146b opens into a pocket channel terminating into the side of the pocket in the distal end of fluid transfer drum 144. The pocket is connectable to cannula 110, such that a fluid connection is made between the at least one channel opening 146b, the pocket channel terminating into the side of the pocket, and cannula lumen 119.

Aspiration device 140 comprises outer casing 148 having a substantially hollow cylindrical shape with an outer diameter, an inner diameter, and a thickness between the outer diameter and the inner diameter. Outer casing 148 has a vertically aligned longitudinal axis coaxial to the longitudinal axis of fluid transfer drum 144. The inner diameter of outer casing 148 is sized to be larger than the diameter of fluid transfer drum 144, defining a space between outer casing 148 and fluid transfer drum 144.

Aspiration device 140 comprises three O-rings 150a, 150b, and 150c, each O-ring having a thickness that fits securely within the space between outer casing 148 and fluid transfer drum 144. O-ring 150a is positioned proximal to the at least one channel opening 146a, O-ring 150b is positioned between the at least one channel opening 146a and the at least one channel 146b, and O-ring 150c is positioned distal to the at least one channel opening 146b. In this manner, the space between outer casing 148 and fluid transfer drum 144 is split into two fluidly isolated chambers that encircle fluid transfer drum 144: proximal liquid chamber 152a between O-ring 150a and O-ring 150b, and distal liquid chamber 152b between O-ring 150b and O-ring 150c. O-rings 150a, 150b, and 150c maintain a leak-roof fit while permitting outer casing 148 and fluid transfer drum 144 to be rotated independently from each other.

Outer casing 148 further comprises port 154a spanning its thickness and opening into liquid chamber 152a, and port 154b spanning its thickness and opening into liquid chamber 152b. A syringe 102 can be mated to each of port 154a and 154b. A liquid connection is thereby established from a syringe 102 mated to port 154a into liquid chamber 152a, whereupon a liquid can enter the at least one channel opening 146a pointed in any direction in the rotation of fluid transfer drum 144 to flow through the centrally located channel and into trocar lumen 129. A liquid connection is also established from a syringe 102 mated to port 154b into liquid chamber 152b, whereupon a liquid can enter the at least one channel opening 146b pointed in any direction in the rotation of fluid transfer drum 144 to flow through the pocket channel into the pocket and into cannula lumen 119.

In FIG. 6, a syringe 102 is depicted mated to proximal open end 136 of stylet 130. In this manner, the contents of syringe 102 can be inserted through proximal open end 136 to travel through stylet lumen 138 and exit out of distal open end 134. Syringe 102 can thereby deliver any suitable compound through stylet 130. In certain embodiments, syringe 102 can deliver an anesthetic, such as lidocaine, such that the anesthetic reduces pain immediately prior to the bone drilling step (FIG. 7A, FIG. 7B), which would ensure anesthetic delivery directly to the site of bone entry.

Figure 8:
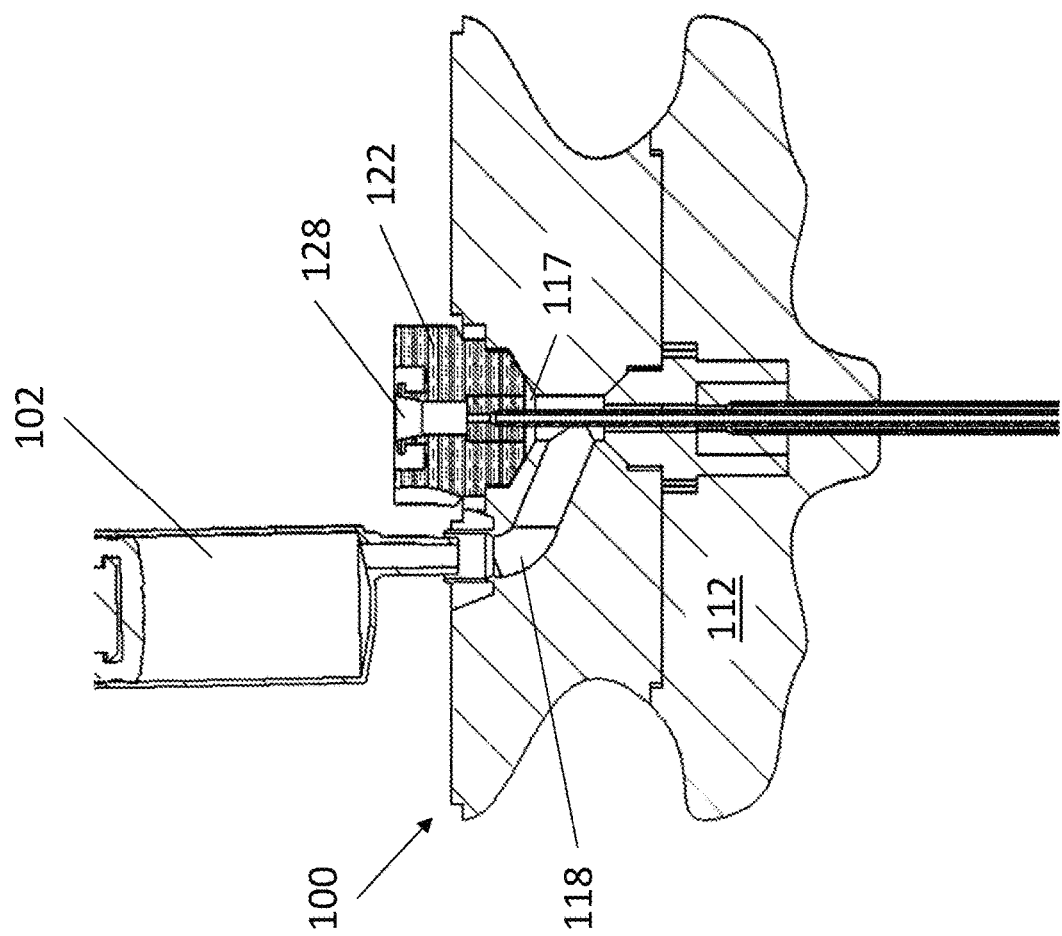
FIG. 8 depicts a syringe mated to the handle portion of an exemplary aspiration device, such as in an aspiration configuration.
Figure 10B:
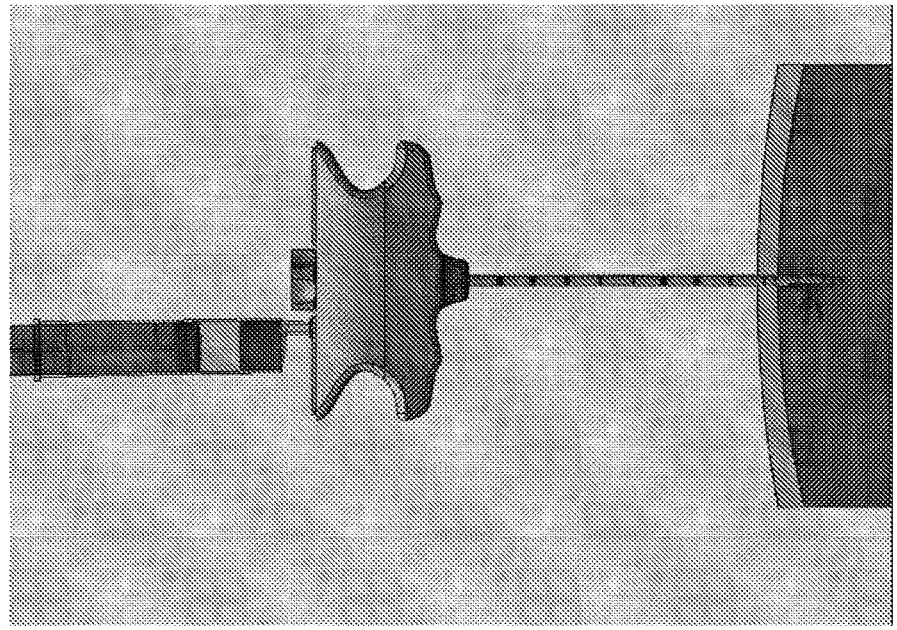
FIG. 10A and FIG. 10B depict an aspiration step using an exemplary aspiration device.
Figure 10A:
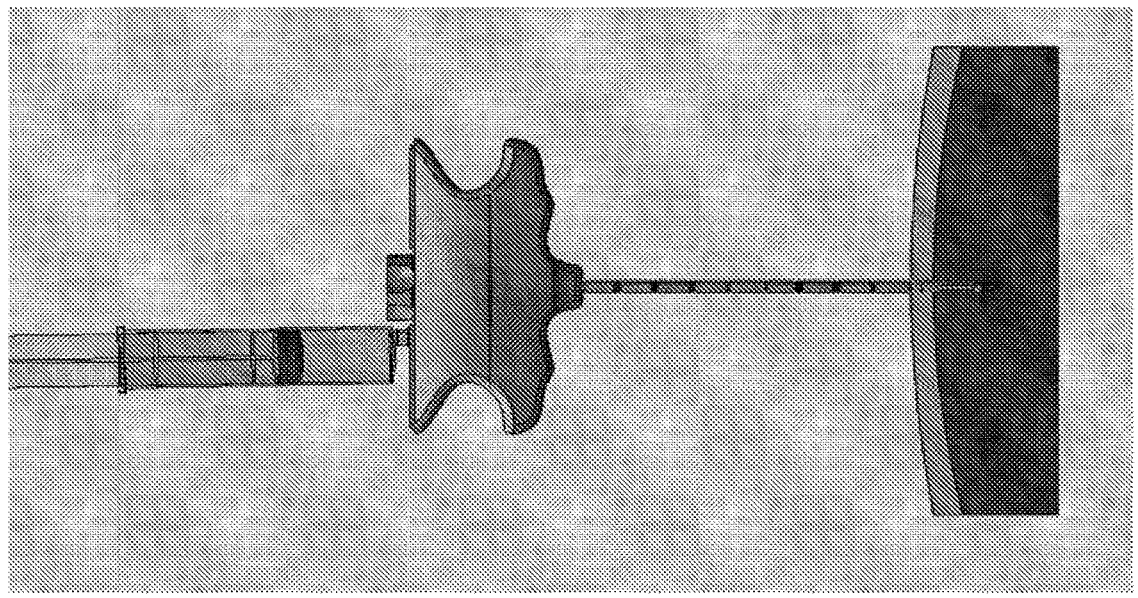

In many aspiration procedures, whole bone anesthesia is performed with intraosseous lidocaine infusion, but it is painful to administer due to the positive pressure change caused by its infusion. Referring now to FIG. 8, the assembled device 100 is depicted with stylet 130 removed as a means to administer an infusion without pain. Stylet 130 may be removed after the assembled device 100 has been successfully drilled into a target site. Removing stylet 130 exposes proximal side lumen 118 and proximal open end 128. Syringe 102 or some other source of solution can be mated to proximal side lumen 118. In this manner, syringe 102 or a source of solution is able to apply an infusion through proximal side lumen 118, through cannula lumen 119, and out of the at least one lateral opening 116 near the distal end of cannula 110 (FIG. 10A, FIG. 10B). In this configuration, proximal open end 128 passively supports pressure equalization in the infusion site by permitting displaced fluid at the infusion site to enter distal tapered end 124, flow into lumen 129 of trocar 120, and push displaced air out of proximal open end 128. Moreover, having a decompression port may allow fluid and medication infusion without the positive pressure levels that may cause pain, obviating the need for lidocaine. Persons having skill in the art will understand that mating a syringe 102 or solution source to proximal open end 128 can have a similar effect, whereupon an infusion can be applied through proximal open end 128, lumen 129 of trocar 120, and out of distal tapered end 124, and proximal side lumen 118 passively supports pressure equalization in the infusion site by permitting displaced fluid at the infusion site to enter the at least one lateral opening 116, flow into cannula lumen 119, and push displaced air out of proximal side lumen 118. Preferably, aspiration is not performed using the assembled device 100 depicted in FIG. 8. Aspirating from one proximal open end without supplying a solution to the opposing proximal open end would lead to the introduction of air or a gas into the opposing proximal open end, opposing lumen, opposing distal or lateral opening, and into the aspiration site as a volume of aspirate is removed. The air or gas would likely be drawn into the blood stream, which may lead to an air or gas embolism and cause injury to a patient.

Figure 9:
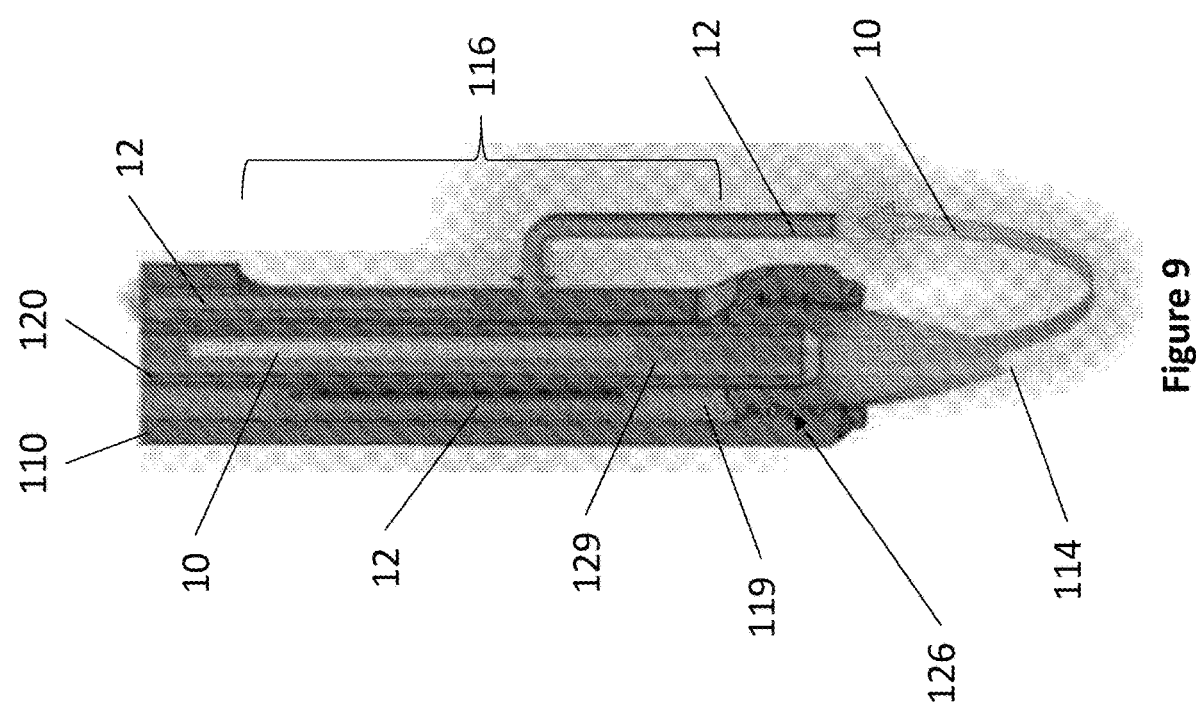
FIG. 9 is a diagram of an exemplary device of the present invention demonstrating aspiration and infusion.

FIG. 9 depicts the distal tip of device 100 having only trocar 120 and cannula 110 to illustrate the pressure modulation concept. As described elsewhere herein, commonly used bone marrow aspiration devices only provide the ability to aspirate, which leads to a pressure change in an aspiration site causing extensive pain and drawing blood into the sample to decompress the vacuum. Device 100 is able to modulate pressure changes by providing at least one additional lumen to the aspiration site. In FIG. 9, exemplary device 100 is capable of administering a solution 10 through lumen 129 of trocar 120 from a solution source, such as the previously described syringe 102. Device 100 is also capable of extracting aspirate 12 through lumen 119 of cannula 110. The distal open end of cannula 110 is sealed by threaded engagement with threaded region 126 of trocar 120, which directs all aspirate 12 into lumen 119 by way of lateral opening 116. The flow of solution 10 and aspirate 12 can be controlled independently, such that administration and extraction can optionally occur concurrently or intermittently as desired. Device 100 is capable of switching between one or more solution sources to administer one or more solutions 10, such as a pharmacological solution from a first reservoir in a first phase, and a saline solution from a second reservoir in a second phase. Device 100 is also capable of modulating the rates of solution 10 administration and/or aspirate 12 extraction.

In some embodiments, syringe 102 can include a syringe mated to proximal side lumen 118 and to proximal open end 128, such as in FIG. 11. In some embodiments, a syringe mated to proximal open end 128 can passively support pressure equalization by permitting the contents of the mated syringe to enter proximal open end 128, flow through lumen 129 of trocar 120, and exit distal tapered end 124 to replace the displaced volume of aspirate. In other embodiments, a syringe mated to proximal open end 128 can actively support pressure equalization, such as by active depression of the syringe mated to proximal open end 128, either by hand or by motorized means. The syringe can dispense a gas or a liquid to support pressure equalization.

Figure 12B:
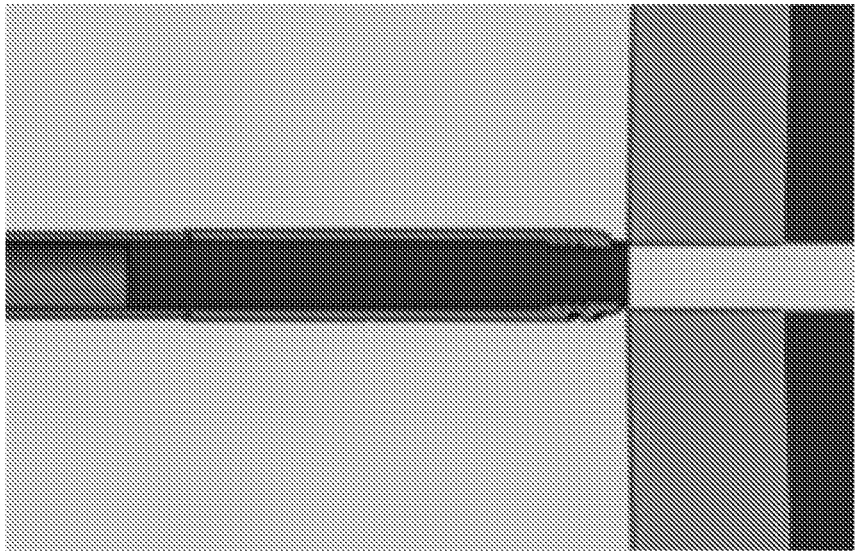
FIG. 12A and FIG. 12B depicts the extraction of a biopsy core using an exemplary aspiration device.
Figure 12A:
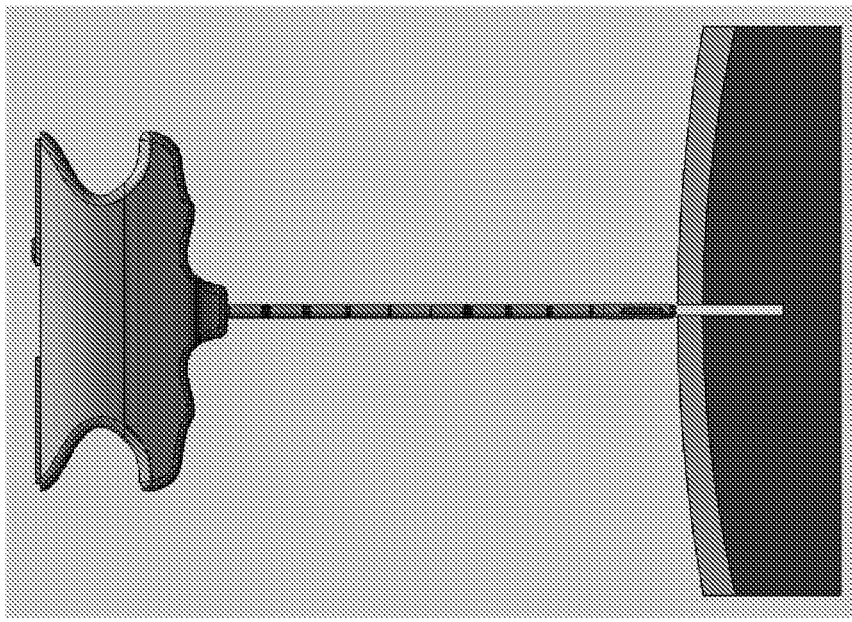

Referring now to FIG. 12A and FIG. 12B, trocar 120 can be removed to leave behind cannula 110. With cannula lumen 119 free from obstruction, cannula 110 can be used to obtain a core biopsy sample. As described elsewhere herein, in certain embodiments, distal open end 114 cannula 110 comprises one or more cutting teeth or flutes, enabling cannula 110 to drive deeper into a biopsy site on its own and capture a biopsy sample. An internal threaded region near distal open end 114 aids in retaining the biopsy sample within cannula lumen 119, whereupon the sample can be easily removed by extracting cannula 110.

Figure 13:
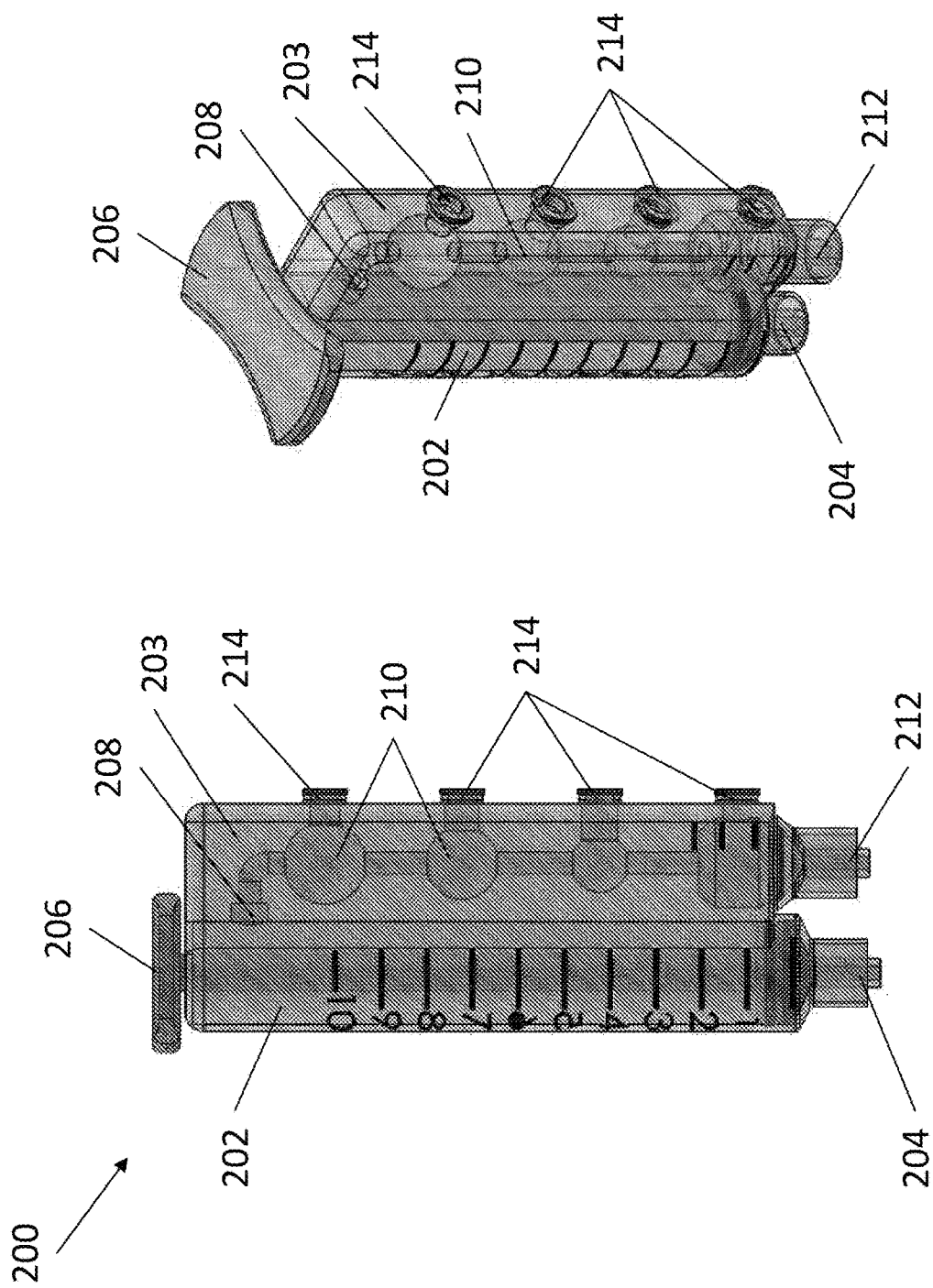
FIG. 13 depicts an exemplary pressure modulating syringe.

Referring now to FIG. 13, an exemplary equalization syringe 200 is depicted. Equalization syringe 200 comprises aspiration chamber 202 and pressure modulating chamber 210. Aspiration chamber 202 is an airtight enclosure comprising plunger 206 and aspiration port 204 at a distal end. Pressure modulating chamber 203 is an airtight enclosure terminating in infusion port 212 at a distal end. Coupling 208 fluidly connects aspiration chamber 202 and pressure modulating chamber 203 at a proximal end. In some embodiments, pressure modulating chamber 203 comprises one or more valves 214. The one or more valves 214 can be used to introduce a solution into pressure modulating chamber 203. Valves 214 can also be used to relieve excess pressure in pressure modulating chamber 203. Valves 214 can be opened manually or passively in response to a predetermined pressure level. In some embodiments, pressure modulating chamber 203 can be subdivided into a plurality of interconnected spherical chambers 210, each having a valve 214, wherein each valve 214 can passively open to relieve pressure in each sphere. For example, the size of an individual chamber 210 may affect the pressure at which valve 214 opens, such that a larger chamber 210 may vent excess gas or liquid at a lower pressure and a smaller chamber 210 may vent excess gas or liquid at a higher pressure. In some embodiments, aspiration port 204 and pressure modulating port 212 are spaced apart such that aspiration port 204 can be mated to a proximal side lumen 118 of an aspiration device 100, and infusion port 212 can be mated to a proximal open end 128 of the aspiration device 100.

In various embodiments, equalization syringe 200 is able to automatically modulate pressure at an aspiration site. As plunger 206 is drawn in a proximal direction, aspiration chamber 202 fills with a volume of aspirate entering from aspiration port 204 and an equal volume of gas or fluid is displaced out of the proximal end of aspiration chamber 202. The volume of gas or liquid exits aspiration chamber 202 through coupling 208 and enters pressure modulating chamber 203 and sequentially through chambers 210, wherein the volume of gas or liquid displaces the contents of pressure modulating chamber 203 to force a volume of infusion gas or liquid out of infusion port 212.

It should be understood that equalization syringe 200 is not limited to the embodiment depicted in FIG. 13, as any mechanism for driving the contents of two adjacent chambers is contemplated. For example, in some embodiments, aspiration chamber 202 and pressure modulating chamber 203 can each have a plunger. The movement of each plunger can be mechanically linked, such as by a lever arm, or by a displacement gas or liquid that passes from one chamber to the opposing chamber. The movement of each plunger can also be electronically linked, such that a sensor may detect a value in one chamber and a controller may reposition the plunger of the opposing chamber automatically. Non-limiting examples of detectable values include the plunger position, the volume of gas or liquid in a chamber, the pressure in a chamber, and the like.

In various embodiments, pressure management at an aspiration site can be performed passively or actively by having an attached device that couples the negative pressure for retrieval and the positive pressure for modulation. This coupling can be done at a −1:1 ratio for maintenance of physiologic pressures in bone, or at any other ratio for a particular desired effect, such as a −1:2 to "flush" the marrow out of the bone. The various embodiments may integrate valves to ensure that positive or negative pressure is not applied to an aspiration site via suction or infusion unless a particular parameter is met. For example, aspiration can be paused if the infusion pressure is not at the desired ratio as the vacuum that is applied. This may be a manually or automatically engaged valve system operating between the syringes and the aspiration and infusion ports leading into an aspiration site.

Figure 14:
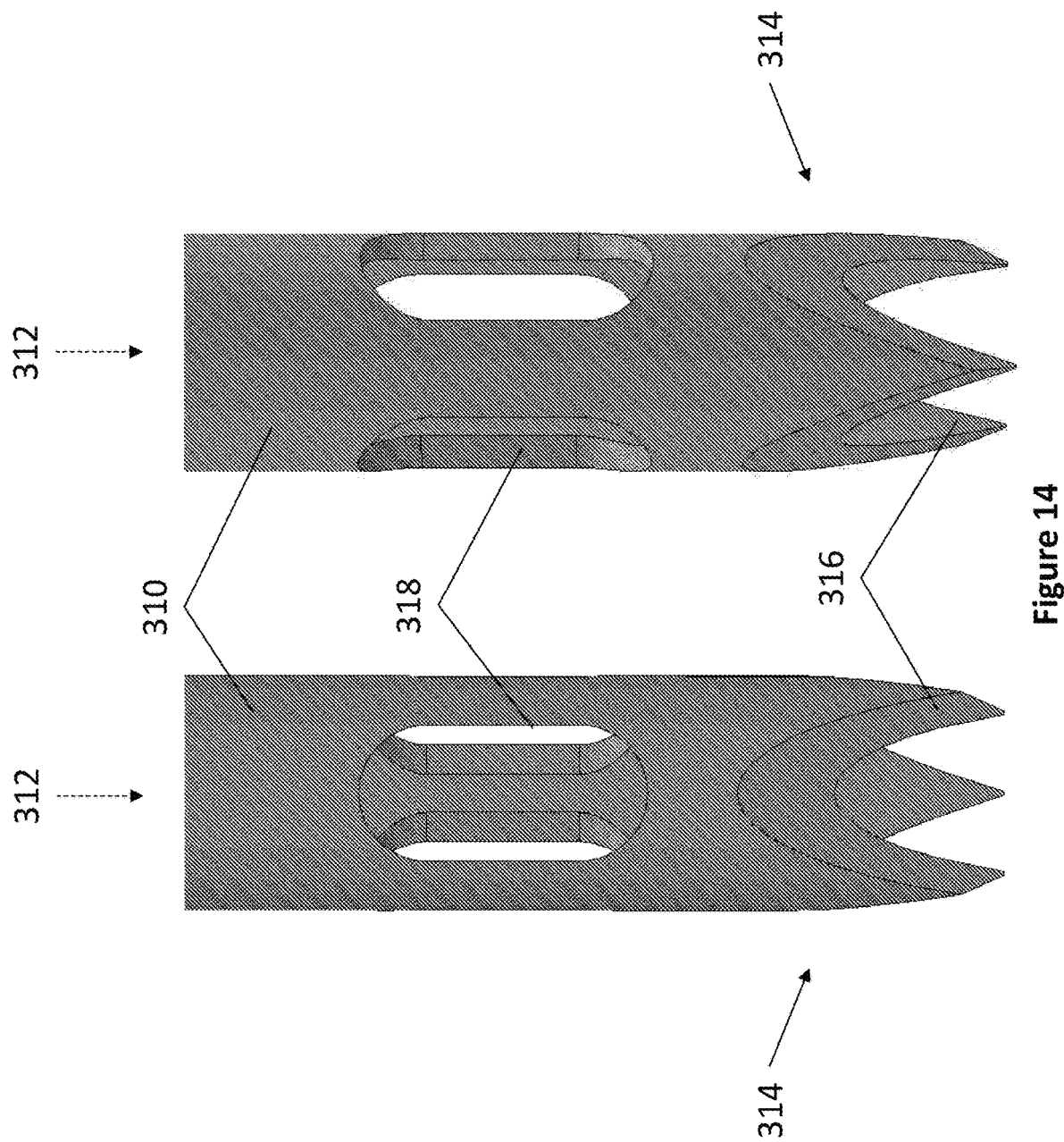
FIG. 14 depicts a cannula of an exemplary aspiration device.

The components of the aspiration devices contemplated herein encompass a plurality of designs. Referring now to FIG. 14, the distal tip of a cannula 310 is depicted. Cannula 310 comprises an elongate hollow tube shape with cannula lumen 312 running throughout. Cannula 310 comprises open distal end 314 having at least one tapered edge 316. Cannula 310 further comprises at least one lateral opening 318 near open distal end 314.

Figure 15B:
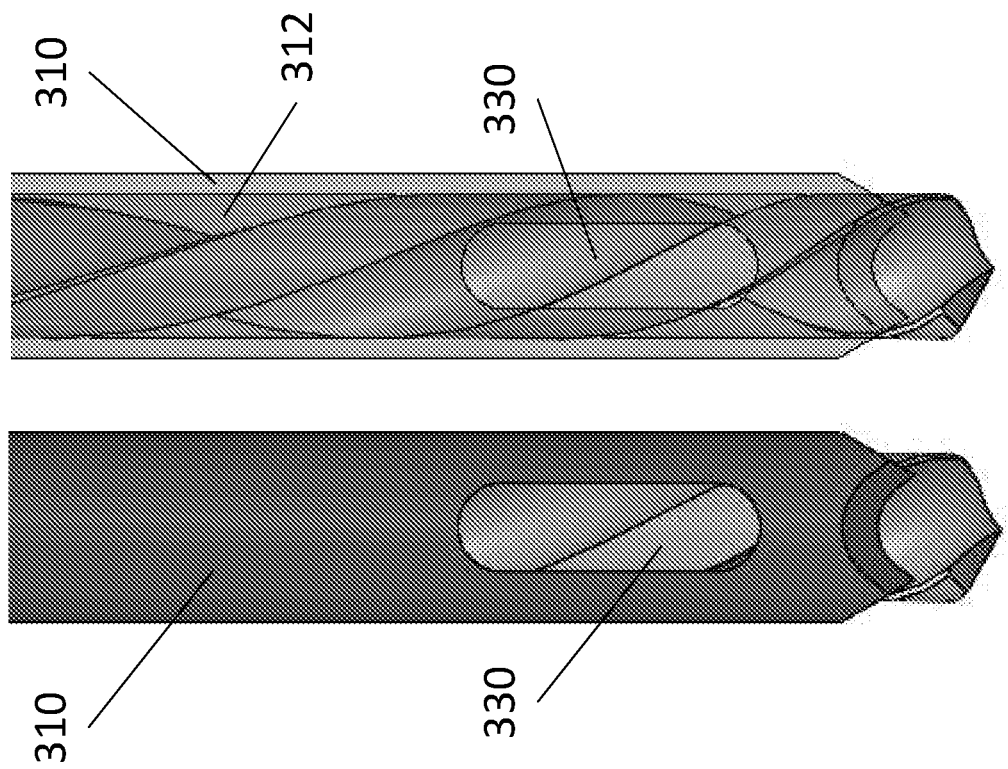
FIG. 15A and FIG. 15B depicts drilling implements compatible with the cannula of an exemplary aspiration device.
Figure 15A:
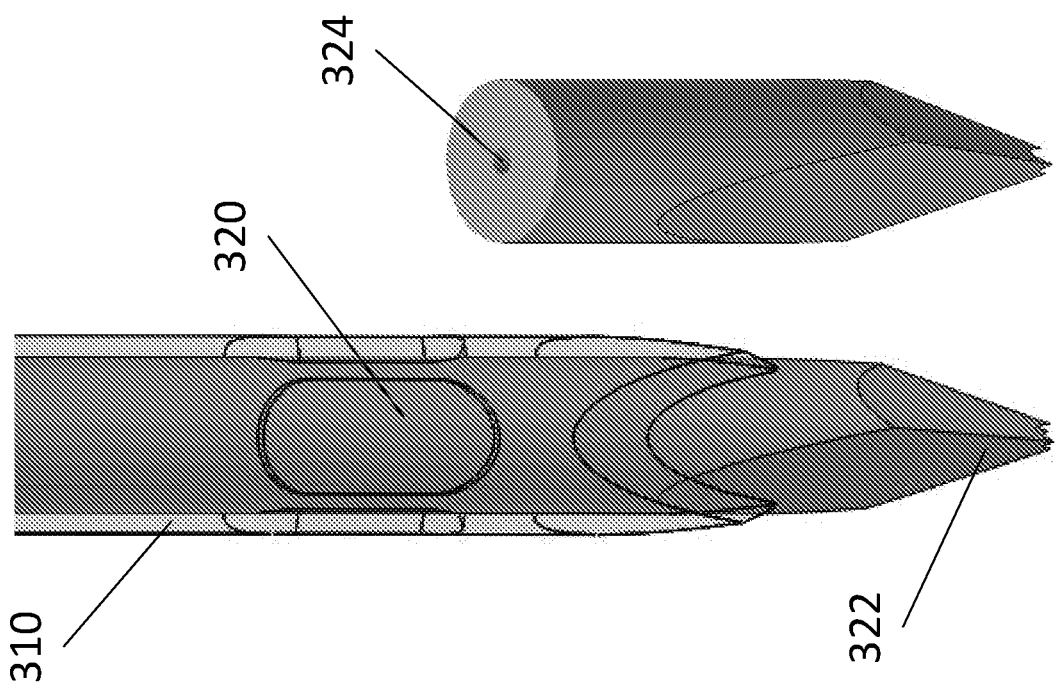

Referring now to FIG. 15A and FIG. 15B, various drilling implements are depicted. Trocar 320 comprises an elongate rod shape sized to fit within cannula lumen 312 and terminates in distal tapered end 322. In some embodiments, trocar 320 comprises lumen 324 running throughout its length. Lumen 324 can be used to directly administer a medicament without the need for a separate stylet. In some embodiments, a drill bit 330 sized to fit within cannula lumen 312 can be used as a trocar. In some embodiments, drill bit 330 can further comprise a lumen running throughout its length capable of administering a medicament similar to lumen 324.

Figure 16:
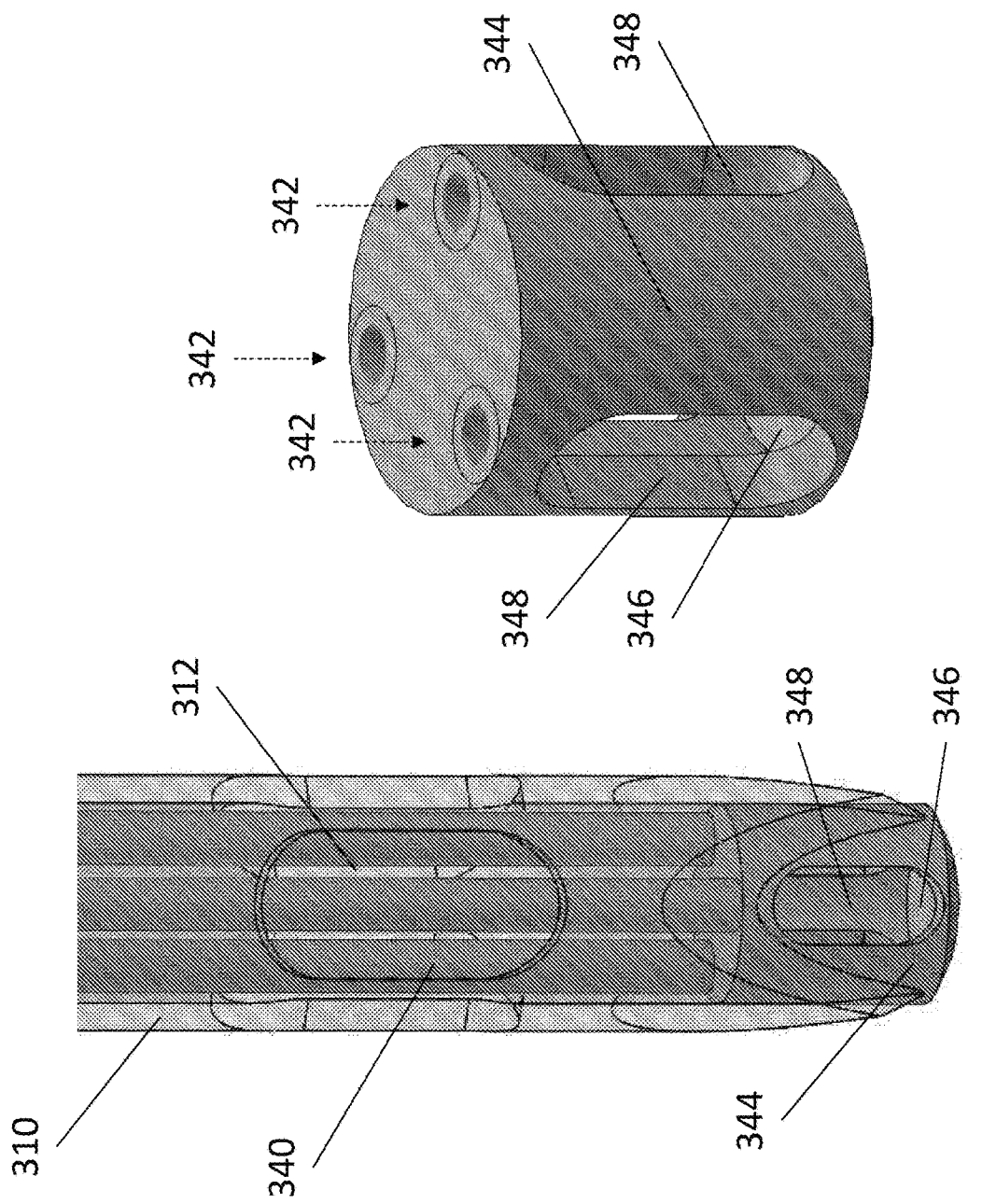
FIG. 16 depicts a multi-lumen stylet compatible with the cannula of an exemplary aspiration device.

Referring now to FIG. 16, an exemplary multi-lumen stylet 340 is depicted. Multi-lumen stylet 340 comprises a plurality of lumens 342 and terminates in stylet tip 344. Stylet tip 344 comprises a substantially cylindrical shape having at least one lateral opening 348 and a closed end 346. The at least one lateral opening 348 can have a length that is as long as the at least one tapered edge 316 of cannula 310. In some embodiments, stylet tip 344 has a diameter that is sized to fit flush within cannula lumen 312. In some embodiments, stylet tip 344 comprises one or more features to enhance fit with cannula lumen 312, such as a threaded region or a gasket. Multi-lumen stylet 340 can be used to direct one or more infusion gases or liquids through each of its lumens into an aspiration site, such that closed end 346 and the at least one lateral opening 348 guide an infusion gas or liquid laterally to bring aspirate closer to lateral openings 318 of cannula 310.

Figure 17:
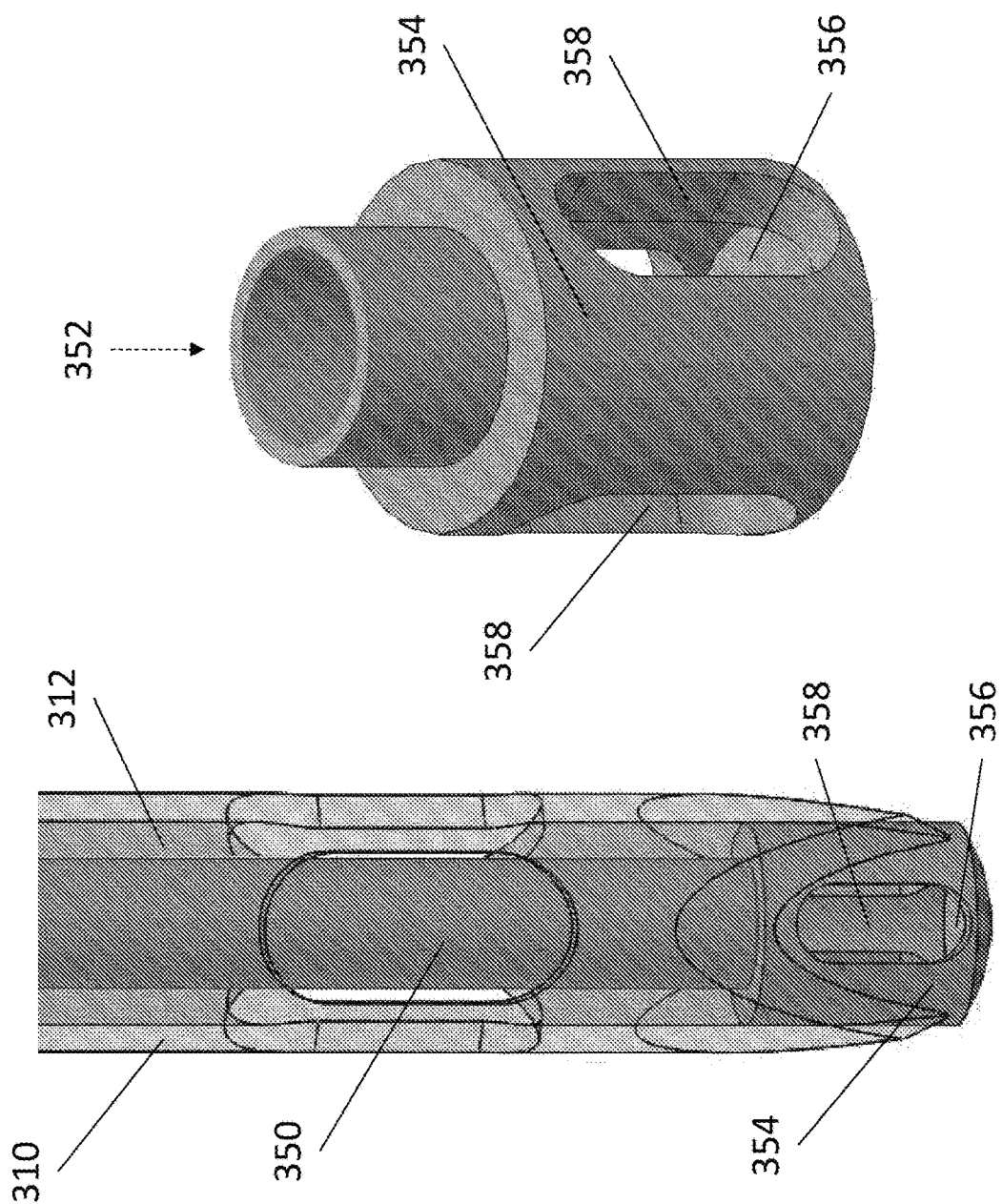
FIG. 17 depicts a single lumen stylet compatible with the cannula of an exemplary aspiration device.

Referring now to FIG. 17, an exemplary single lumen stylet 350 is depicted. Single lumen stylet 350 comprises a single elongate tube having a lumen 352 running throughout and terminates in stylet tip 354. Single lumen stylet 350 preferably has an outer diameter that is narrower than the inner diameter of cannula lumen 312, such that a gap forms between the two to permit the transfer of a fluid. Stylet tip 354 comprises a substantially cylindrical shape having at least one lateral opening 358 and a closed end 356. The at least one lateral opening 358 can have a length that is as long as the at least one tapered edge 316 of cannula 310. In some embodiments, stylet tip 354 has a diameter that is sized to fit flush within cannula lumen 312. In some embodiments, stylet tip 354 comprises one or more features to enhance fit with cannula lumen 312, such as a threaded region or a gasket. Single lumen stylet 350 can be used to direct an infusion gas or liquid into an aspiration site, such that closed end 356 and the at least one lateral opening 358 guide an infusion gas or liquid laterally to bring aspirate closer to lateral openings 318 of cannula 310.

Figure 18:
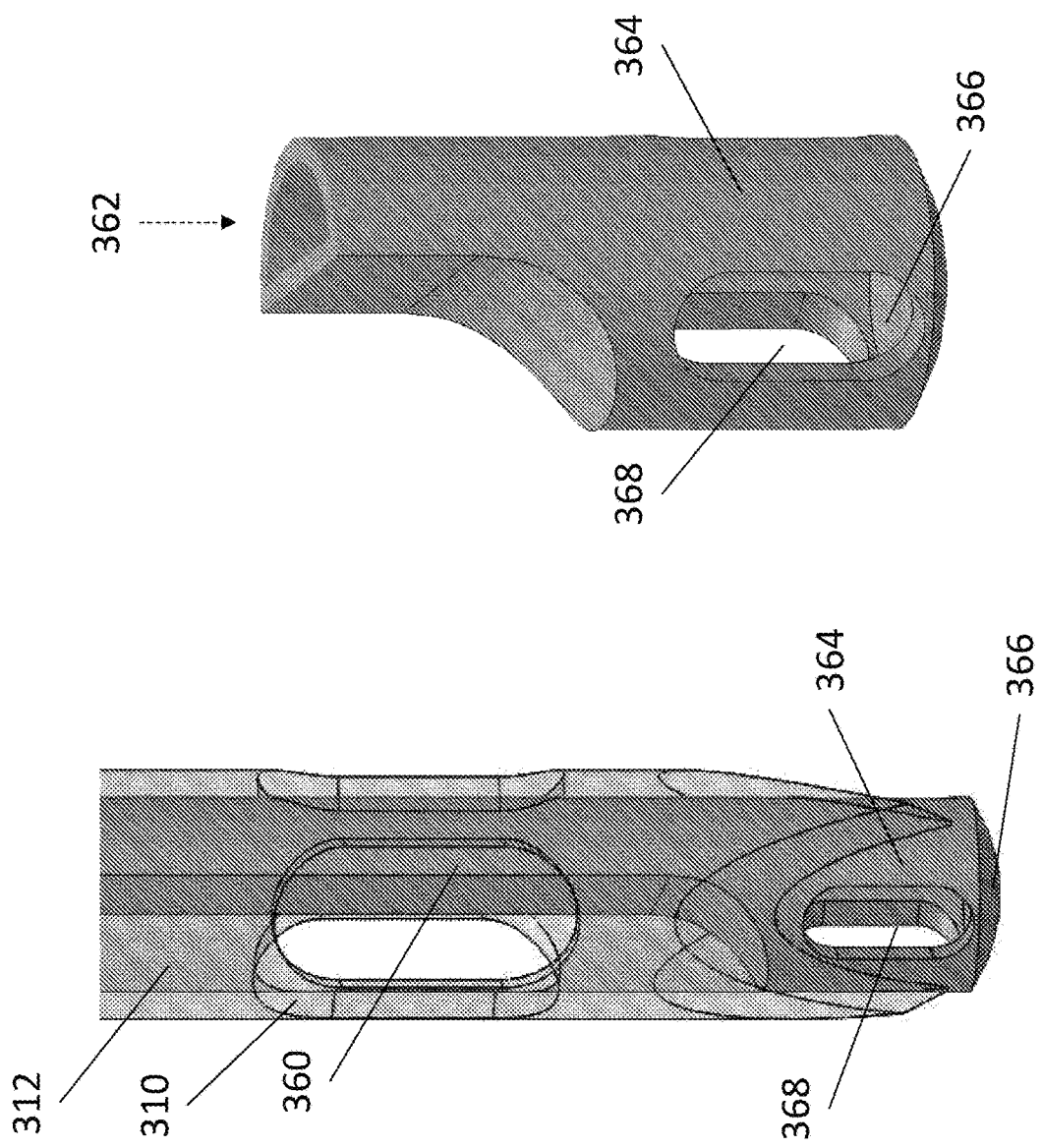
FIG. 18 depicts an asymmetrical lumen stylet compatible with the cannula of an exemplary aspiration device.

Referring now to FIG. 18, an exemplary asymmetrical lumen stylet 360 is depicted. Asymmetrical lumen stylet 360 comprises a single elongate conduit having a lumen 362 running throughout and terminates in stylet tip 364. The conduit shape of asymmetrical lumen stylet 360 has a cross sectional area that is smaller than cannula lumen 312, such that a gap forms between the two to permit the transfer of a fluid. The conduit can have any suitable cross sectional shape, such as a circle, oval, square, rectangle, triangle, and the like. In some embodiments, the conduit has a circular segment cross sectional shape, such that the cross sectional shape has an arced side that can fit flush against the inner surface of cannula lumen 312, and at least one flat side facing away from the arced side. In this manner, asymmetrical lumen stylet 360 has the feature of being able to selectively block at least one lateral opening 318 of cannula 310 using the arced side and thereby control the direction of fluid transfer. Stylet tip 364 comprises a substantially cylindrical shape having at least one lateral opening 368 and a closed end 366. The at least one lateral opening 368 can have a length that is as long as the at least one tapered edge 316 of cannula 310. In some embodiments, stylet tip 364 has a diameter that is sized to fit flush within cannula lumen 312. In some embodiments, stylet tip 364 comprises one or more features to enhance fit with cannula lumen 312, such as a threaded region or a gasket. Asymmetrical lumen stylet 360 can be used to direct an infusion gas or liquid into an aspiration site, such that closed end 366 and the at least one lateral opening 368 guide an infusion gas or liquid laterally to bring aspirate closer to lateral openings 318 of cannula 310.

Figure 19:
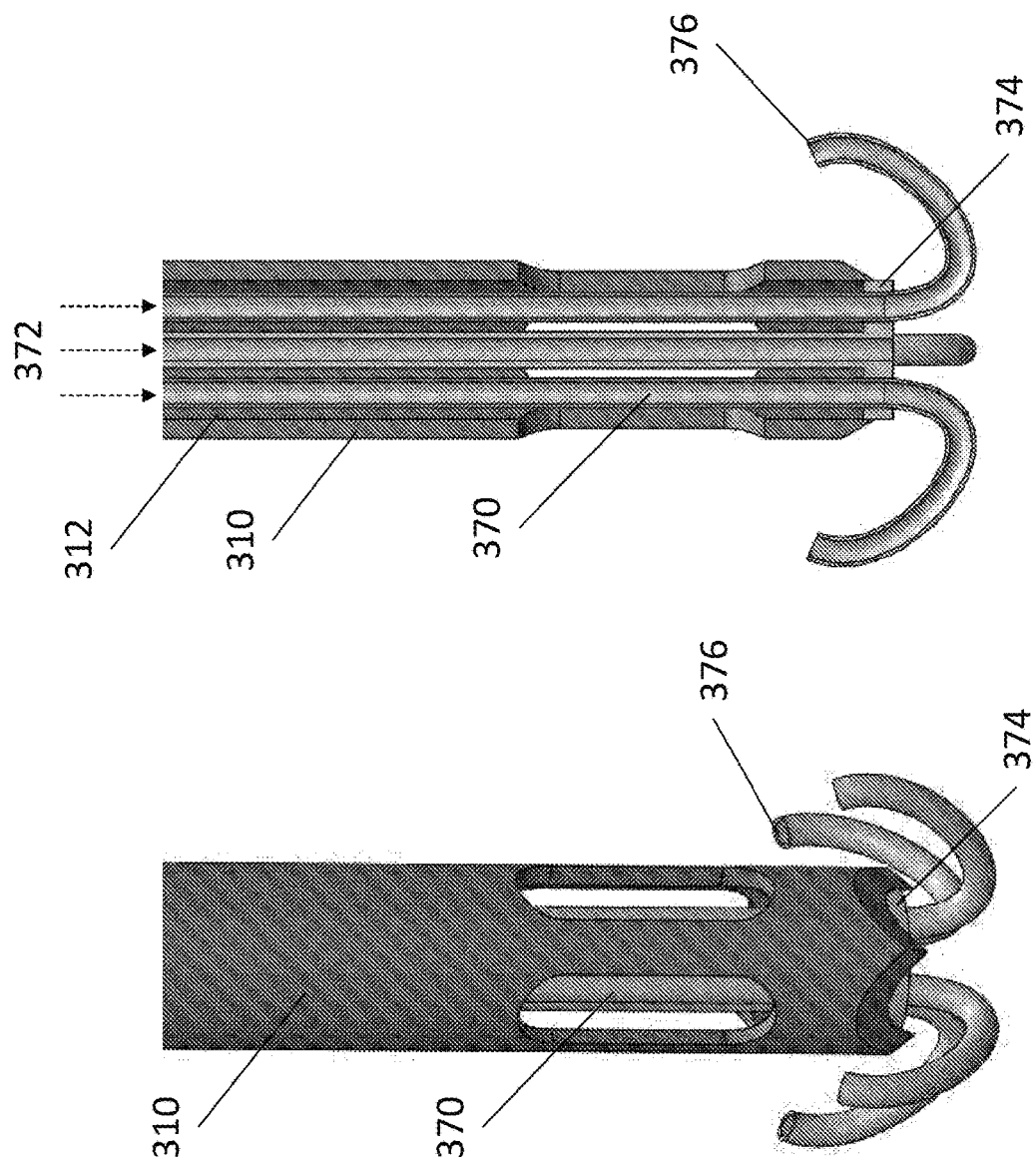
FIG. 19 depicts a directional lumen stylet compatible with the cannula of an exemplary aspiration device.

Referring now to FIG. 19, an exemplary directional lumen stylet 370 is depicted. Directional lumen stylet 370 comprises a plurality of individual lumens 372 secured to stylet tip 374. Each of the lumens 372 extend past stylet tip 374 and terminate in an open end 376 positioned at any suitable distance from a lateral opening 318. Open end 376 can be directed to face any direction. In some embodiments, open end 376 can be actuated to change its direction or its distance from a lateral opening 318. Open end 376 can also be actuated to macerate tissue at an aspiration site. In some embodiments, directional lumen stylet 370 is constructed at least in part from a shape-memory material such as nitinol, permitting each of the lumens 372 to adopt a predetermined shape after being inserted through cannula lumen 312. Stylet tip 344 comprises a substantially cylindrical shape having a diameter that is sized to fit flush within cannula lumen 312. In some embodiments, stylet tip 374 comprises one or more features to enhance fit with cannula lumen 312, such as a threaded region or a gasket. Directional lumen stylet 370 can be used to direct one or more infusion gases or liquids through each of its lumens 372 in any desired direction. In some embodiments, one or more of the lumens 372 can be used to transfer an aspirate from a site of aspiration.

The various components of the present invention described above can be constructed using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. Components substantially comprising glass can be cut from larger pieces of glass. In some embodiments, the devices may be made using 3D printing or other additive manufacturing techniques commonly used in the art.

Methods of Aspiration

The present invention further includes enhanced methods of biopsy aspiration that increase cell yield and reduce pain. The methods combine aspiration with the administration of a solution, and can be performed with the aspiration devices of the present invention described elsewhere herein.

The methods of the present invention are based in part on the surprising and unexpected discovery that the administration of lidocaine using the novel devices of the present invention in a BMA procedure increased stem cell yields compared to a control method by more than 200%. When lidocaine was administered using a standard BMA device, the stem cell yield was drastically reduced, as if the cells were washed away from the site of administered lidocaine. However, when the lidocaine was administered in one part of the bone and the aspiration occurring remotely at a second part of the bone, the stem cell yield was greatly increased.

The methods of the present invention are also based on the ability of the aspiration devices to maintain a relatively physiologic pressure within the bone during aspiration. This serves two purposes: 1) the vacuum/pressure gradient in other devices runs from the syringe to the device to the marrow to the blood, thereby aspirating in less viscous blood and contaminating the aspirate, while the aspiration devices pass the vacuum/pressure from the syringe to the device to the marrow back to the syringe, excluding mature blood cells from the aspirate, and while no affirmative standard is available for venous contamination, doubling the CFU per $10^5$ cells demonstrates a significant reduction in hemodilution; and 2) reduction of the vacuum decreases pain caused during aspiration since bone is exquisitely sensitive to pressure changes often accompanied by pain.

Furthermore, the administration of lidocaine serves to decrease patient pain as it is a known anesthetic, blocking all nerve transduction, and has been shown to be able to create whole bone anesthesia during intraosseous infusions.

Figure 20:
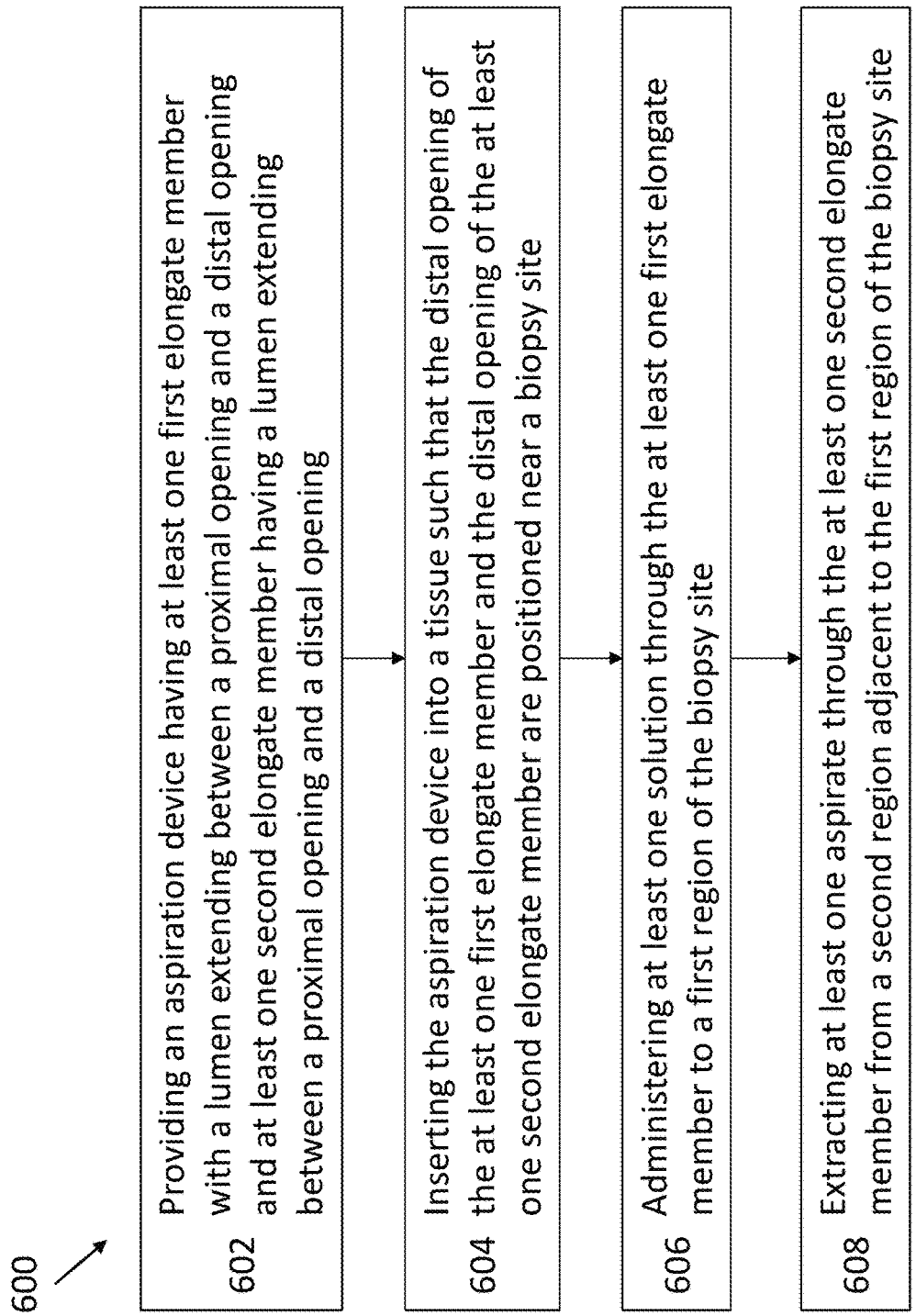
FIG. 20 depicts an exemplary method of cell acquisition.
Figure 21:
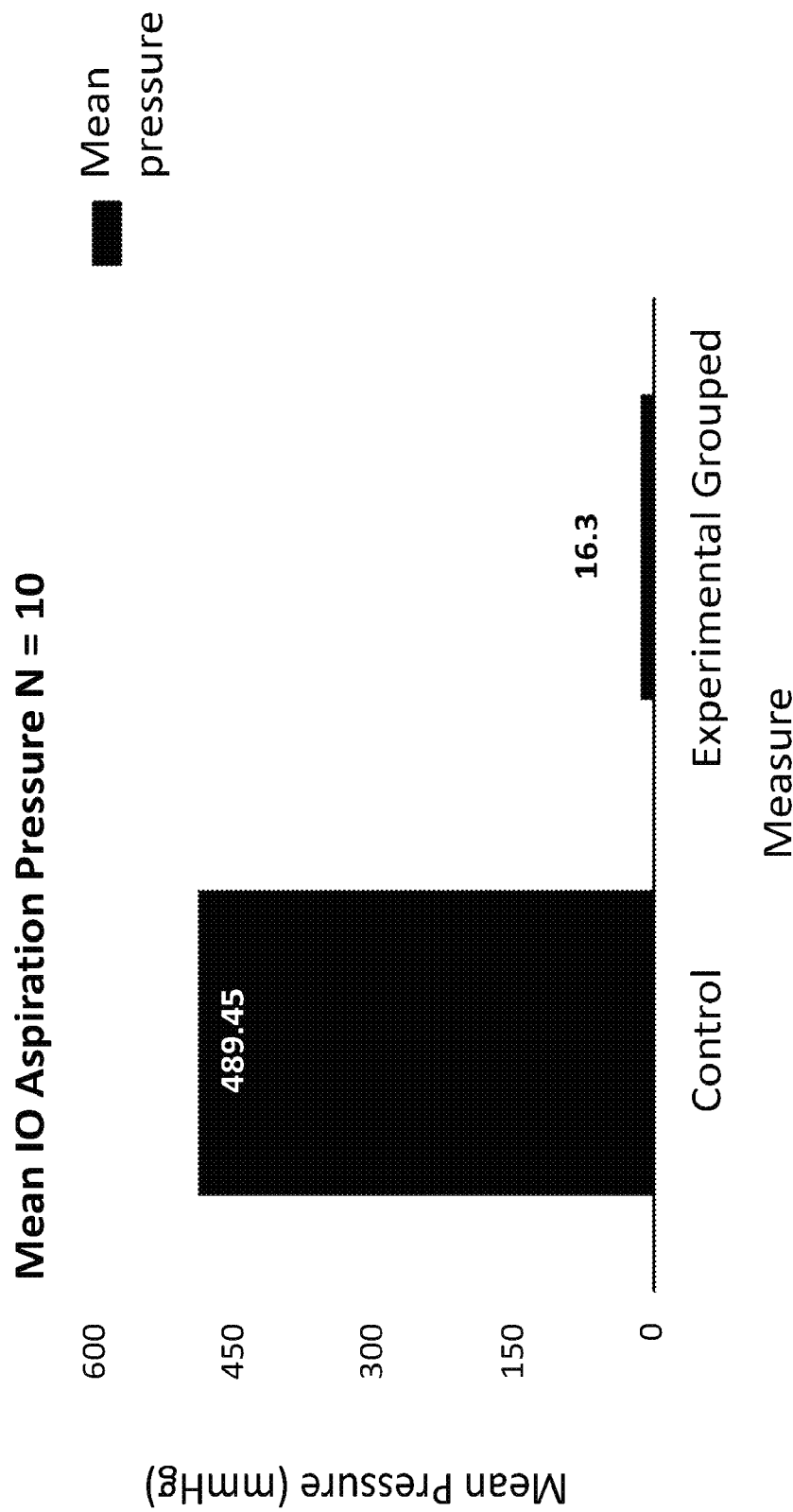
FIG. 21 is a bar graph depicting bone marrow vacuum pressure in control (left) versus an exemplary aspiration device of the present invention (right). The exemplary aspiration device of the present invention decreased pressure by 97%.
Figure 22:
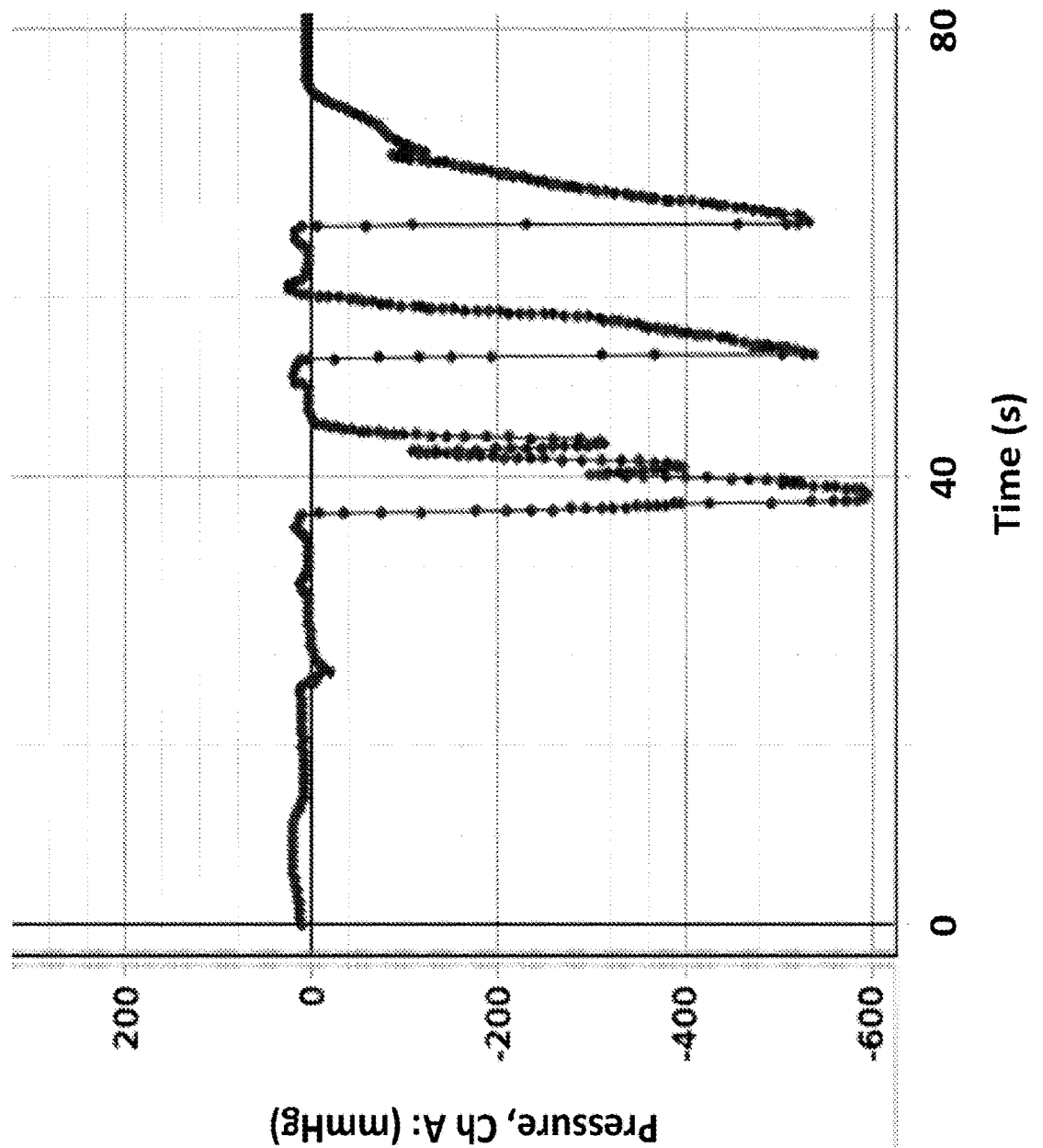
FIG. 22 depicts pressure measurements during three successive control aspirations made with a 10 cc syringe and a standard end-hole needle. Note the min peak of 600 mmHg (perfect vacuum is −760 mmHg and near the negative pressure at which blood cavitates, when gas spontaneously comes out of solution with damaging effects).
Figure 23:
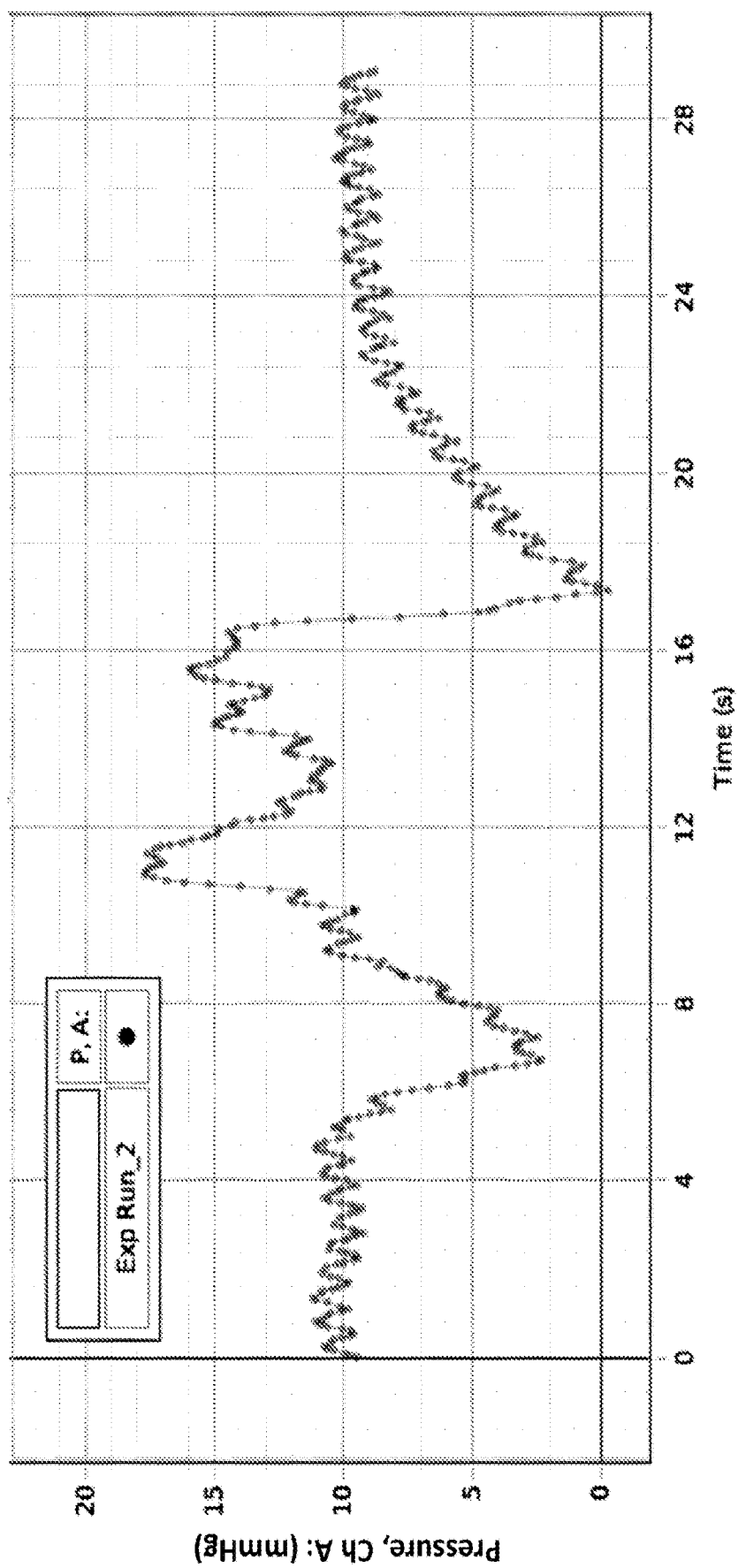
FIG. 23 depicts an experimental run using an exemplary aspiration device of the present invention. Note the different scale, allowing visualization of the normal positive perfusion pressure of bone (~10 mmHg) with small peaks and valleys at baseline representing the cardiac pulsations transmitted to the bone. This is a single experimental aspiration with an exemplary aspiration device combined with an equalization syringe. Note the near-perfect equalization of the pressure during aspiration.
Figure 24:
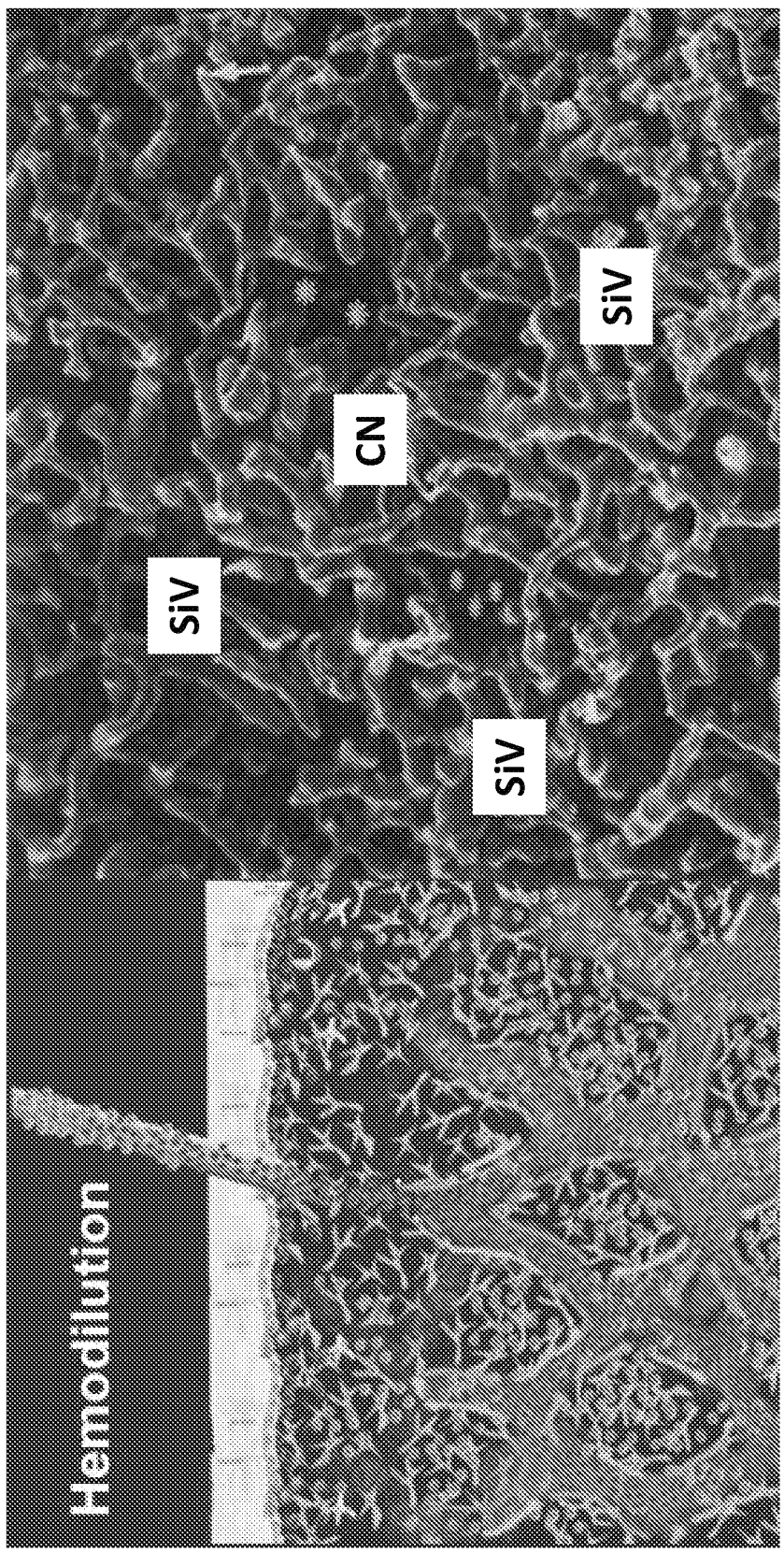
FIG. 24 depicts the microanatomy of bone marrow. The right figure is an electron micrograph of a vascular cast of bone marrow; the tubular structures are tiny blood-filled sinusoids and venules. The blue stars are the space between where the stem-cells are anchored to the parenchyma. When a needle is placed in the bone it breaks into these vascular spaces. When suction is applied, blood flows into the needle from these tubes rather than anchored stem cells. This is the reason for blood contamination and why current bone marrow aspirations only pull blood rather than being a true stem cell harvest.
Figure 25:
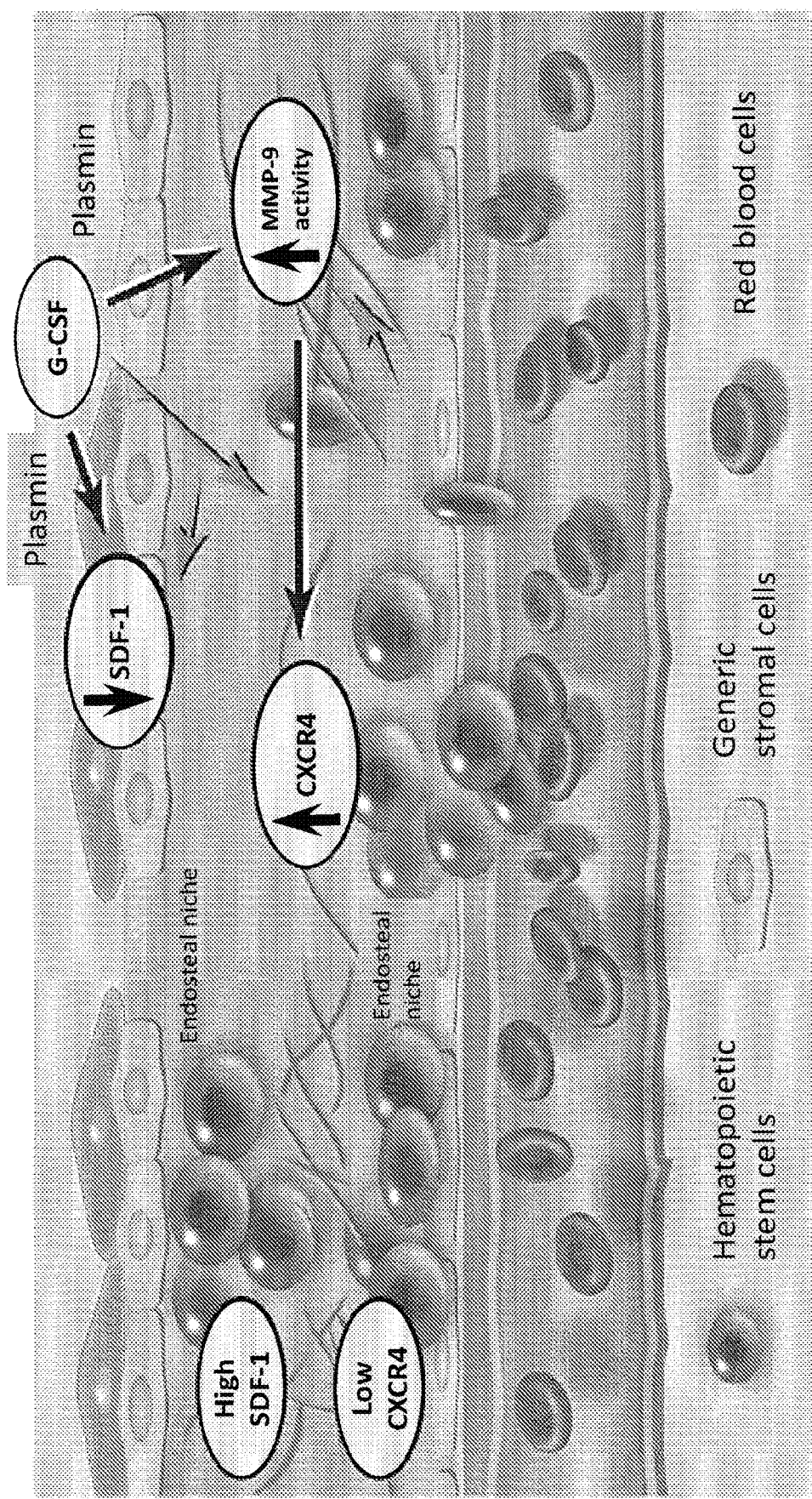
FIG. 25 depicts a diagram of one molecular pathway showing stem cell mobilization using augmentation with intraosseous administration of drugs, which achieve initial peak concentrations directly at the site of action, much higher concentrations than would otherwise be possible with other routes of administration. Drug administration causes cells to come out of their niche into these vascular spaces, allowing them to be harvested in greater number.
Figure 26:
FIG. 26 depicts a picture of a 3D volume of a CT scan of a porcine model with an exemplary aspiration device inserted in the bone and radiopaque contrast injected into the infusion port, demonstrating the medication diffusing throughout a large portion of the bone.

Referring now to FIG. 20, an exemplary method 600 is depicted. Method 600 begins with step 602 of providing an aspiration device having at least one first elongate member with a lumen extending between a proximal opening and a distal opening and at least one second elongate member having a lumen extending between a proximal opening and a distal opening. In step 604, the aspiration device is inserted into a tissue such that the distal opening of the at least one first elongate member and the distal opening of the at least one second elongate member are positioned near a biopsy site. In step 606, at least one solution is administered through the at least one first elongate member to a first region of the biopsy site. In step 608, at least one aspirate is extracted through the at least one second elongate member from a second region adjacent to the first region of the biopsy site.

The insertion step can be performed using any suitable means. For example, the aspiration device can be inserted using a trocar having a tapered distal end or using a drill bit, as described elsewhere herein. The insertion step can be supplemented with the infusion of an anesthetic to reduce pain, such as in FIG. 7A and FIG. 7B. The tissue can be any tissue containing cells of interest, such as adipose tissue, bone marrow tissue, peritoneal cavity, and the like. However, the method can also be used to mobilize cells within any tissue of interest and is therefore applicable to all anatomic sites, such as the inner ear for auditory hair cells, the central nervous system for neural, axonal, or supportive cells, the eye for retinal cells, or any of the various skeletal muscle, skin, teeth, heart, gut, liver, and other organs and tissues. The cells of interest can be any suitable cell, such as a stem cell, stromal cell, gland cell, nerve cell, fat cell, germ cell, and the like. The first region and the second region can be immediately adjacent, or separated by a distance between 1 mm and 1000 mm.

In some embodiments, the administration step and the extraction step are performed concurrently. In this manner, an amount of solution is constantly administered as an amount of aspirate is extracted, such that the pressure within the tissue is substantially constant. In one embodiment, the simultaneous action of solution administration and aspirate extraction can be driven by actively pumping both mediums in their respective sites. In one embodiment, the simultaneous action of solution administration and aspirate extraction is driven by fluid pressure within the tissue. For example, active pumping of only the solution into the first region increases the pressure within the tissue, wherein the pressure increase drives the flow of aspirate into the second region. In another example, active pumping out of the tissue (suction) of only the aspirate from the second region decreases the pressure within the tissue, wherein the pressure decrease drives the flow of solution into the first region. All of the abovementioned mechanisms have been shown to decrease aspiration site pressure change in a porcine model. Since pressure can be associated with patient pain, the methods preferably effects a mean pressure change of about 15 to 50 mmHg compared to control values of about 400 to 700 mmHg.

In some embodiments, the extraction step follows the administration step after a delay. A delay enables an administered solution some time to permeate the tissue and to apply any number of therapeutic or cell mobilizing effects to the tissue before the extraction of aspirate containing one or more cells. The multiple elongate members of the devices of the present invention allow for mitigation of pressure changes that may be incurred during infusion and aspiration. The amount of solution administered can be less than or substantially equal to the amount of expected aspirate, such as an amount between 1 mL and 15 mL of solution depending on the doses required by the pharmacokinetics of the solution, which may be based around the weight of a patient. The delay time can be any suitable time, such as a period between 30 seconds and 120 minutes.

In some embodiments, the administration step and the extraction step can be performed using at least one elongate member. For example, the method can comprise the steps of providing an aspiration device having at least one elongate member with a lumen extending between a proximal opening and a distal opening; inserting the aspiration device into a tissue such that the distal opening of the at least one elongate member is positioned near a biopsy site; administering at least one cell mobilizing composition through the at least one elongate member into the biopsy site; and extracting at least one aspirate through the same elongate member.

As described elsewhere herein, the administered solution can increase cell yield. The administered solution can work through one or more mechanisms, including but not limited to: mobilizing cells from their native milieu; blocking the inhibition of cell departure; decreasing adhesion of cells to their surrounding environment; and modulating the neural or cellular control that dictate the stability, ingress, or egress of cells from their milieu. Compared to traditional procedures, the methods of the present invention can increase cell yields by at least 50%, at least 100%, at least 150%, at least 200%, at least 250%, at least 300%, or more. The solution can include any suitable composition that can augment cell yield by modulating the nervous system regulation of cell mobilization, by decreasing adherence to the native tissue or creating a cell mobilizing effect. Cells may be mobilized into the surrounding extracellular milieu/matrix which may include the surrounding vascular space; in the case of bone marrow, this may be into the surrounding capillary bed and sinusoids. The solution may include small molecules, peptides, polypeptides, nucleic acids, and carbohydrates. Non-limiting categories of agents that may be used include currently known and yet to be discovered classes of proteins and receptors known to control the movement of cells out of tissue or retention of cells in tissue (See Table 1). These may include combinations, for example inhibition of $\alpha_9\beta_1$ by BOP (antibody or other small molecule selective inhibiter) and AMD3100 in combination. These include broad categories such as: modulation of the integrin family such as the VLA-4 molecule inhibitors firategast, UNII-OJY3SK9H5F, and BIO5192; modulation of the CXCL12/CXCR4 interaction such as the CXCR4 inhibitor plerixafor; modulation of the CXCR7 molecule; CXCL12 analogues; modulation of the nerve/stem cell interaction such as the dopamine receptors (1-5 subtypes) and noradrenergic alpha and beta receptors and all such receptors for the catecholamines, their precursors and derivatives; modulators of their receptors or modulators of the uptake of the neurotransmitters from the synapse/site of action; catecholamine degradation inhibitors such as inhibitors of catechol-O-methyltransferases (COMT) or amination by monoamine oxidases (MAO) enzymes; modulators of downstream cascade of catecholamine receptors such as adenylate cyclase and alternative phosphoinositide 3-kinase (PI3K)/Akt pathways; agonists and blockers of catecholamine receptors a1, a2, b1, b2, and b3; catecholamine precursors such as L-Phenylalanine, L-Tyrosine, and L-DOPA; dopamine agonists such as aripiprazole, phencyclidine, quinpirole, salvinorin A, apomorphine, bromocriptine (Parlodel), cabergoline (Dostinex), ciladopa, dihydroxazine, dinapsoline, doxanthrine, epicriptine, lisuride, pergolide, piribedil (Pronoran and Trivastal), pramipexole (Mirapex and Sifrol), propylnoraporphine, quinagolide (Norprolac), ropinirole, rotigotine, roxindole, sumanirole, fenoldopam selective for dopamine receptor D1, cocaine, amphetamines; dopamine reuptake inhibitors such as buproprion altropane (O-587), Amfonelic acid (WIN 25978), Amineptine (has a reasonable degree of selectivity for dopamine over norepinephrine reuptake inhibition), BTCP (GK-13), 3C-PEP (extremely potent and selective for dopamine transporter), DBL-583, Difluoropine (O-620), GBR-12783, GBR-12935, GBR-13069, GBR-13098, GYKI-52895, Iometopane (β-CIT, RTI-55), Methylphenidate, Ethyphenidate, Modafinil, Armodafinil, RTI-229, Vanoxerine (GBR-12909), Haloperidol, Chlorpromazine, Eticlopride, Pimozide, Chlorpromazine, Eticlopride; desipramine and other drugs that inhibit the reuptake of norepinephrine; DRD1, DRD2, DRD3, DRD4, DRD4 receptor agonists, and antagonists such as eticlopride; nicotine; b2-adrenergic agonists such as clenbuterol; alpha9 integrin agonists; BOP, N-(Benzene-sulfonyl)-L-prolyl-L-O-(1-pyrrolidinylcarbonyl)tyrosine); VLA-4 antagonists such as trans-4-[1-[[2-(5-Fluoro-2-methylphenylamino)-7-fluoro-6-benzoxazolyl]acetyl]-(5S)-[methoxy(methyl)amino]methyl-(2S)-pyrrolidinylmethoxy]cyclohexanecarboxylic acid, natalizumab, and BIO5192; matrix metalloproteinases and their inducers such as Me6TREN; prolyl hydroxylase inhibitors such as dimethyloxallyl glycine (DMOG); the chemokine GRObeta; sulfated colominic acid; beta-chemokine CCL15; panax notoginseng saponins; VEGF; ALT-1188; P2RY14 agonists such as MRS2690; UDP-glucose; gamma-tocotrienol; TGF β, TGF-β1, and Substance P; modulation of the adhesion molecules such as VCAM-1; interaction with the integrins such as VLA-4 (α9β1); G-protein coupled receptors such as P2Y purinoceptor-14; S1P-1 modulators including ACT-128800, SEW2871, GSK2018682, FTY720, MRS 2690, and dopamine; various endocrine targets such as NOTCH protein (parathyroid hormone); granulocyte colony-stimulating factor (G-CSF) and analogs (filgrastim); PEGylated and glycosylated versions of G-CSF; granulocyte macrophage colony-stimulating factor (GM-CSF); macrophage colony stimulating factor (M-CSF); tyrosine kinase 3 (FLT-3); ancestim; stem cell factor; AMD3100; TG-0054; KRP203; 4F-benzoyl-TN14003; POL6326; P2G, a mutant protein of SDF-1β; CTCE-0021; CS549, a pepducin such as ATI-2341; a cytokine (such as interleukin-1, interleukin-3, interleukin-6, interleukin-7, interleukin-11, interleukin-12); a metalloproteinase; a serine protease; a cysteine protease; a peptidase; a chemokine; and the like. Multiple chemotherapies can also be administered as currently administered intravenously, such as cyclophosphamide.

TABLE 1

Cell mobilizing candidates.

| GROUP | Agent | Mechanism |
|---|---|---|
| A | CXCR4/CXCL12/CXCR7 group (agonist and antagonists) | |
| | GSK812397 | Orally bioavailable noncompetitive CXCR4 antagonist. Derived from amb 070 |
| | AMD070 | Orally bioavailable non-cyclam CXCR4 antagonist derived from plerixafor |
| | KRH-3955 | Orally bioavailable, non-cyclam, non-peptide small moledule CXCR4 antagonist designed from KRH 1636 |
| | BKT-140 | 14 residue polypeptide antagonist of CXCR4 |
| | FC131 | Developed by molecular size reduction of the 14 resident T140 CXCR4 antagonist |
| | WZ811 | Lead candidate drug in a new class of CXCR4 antagonists that contain two aromatic amine moieties connected by a para-xylylene group |
| | ALX-0651 | |
| | NOX-A12 | L-enantiomeric RNA oligonucleotide (Spiegelmer) that binds and neutralizes CXCL12 |
| | MDX-1338 | Human antibody that targetse CXCR4 |
| | AMD3100/plerixafor | CXCR4 antagonist |
| | TG-0054 | CXCR4 antagonist |
| | KRP203 | CXCR4 antagonist |
| | 4F-benzoyl-TN14003 | CXCR4 antagonist |
| | POL6326 | CXCR4 antagonist |
| | P2G, a mutant protein of SDF-1β | High antagonistic activity against CXCR4; high potency in enhancing ischaemic angiogenesis and blood perfusion. |
| | CXCL12 (SDF-1) | Ligand of CXCR4 |
| | CTCE-0021 | CXCR4 agonist peptide, |
| | CX549 | CXCR4 Antagonist |
| | CXCR4 pepducins (e.g., ATI-2341) | Works on G Protein of the CXCR4 receptor CXCR4 agonist (CXCR4-targeted therapeutics using lipopeptide G protein-coupled receptor (GPCR) modulators called pepducins |
| B | S1P-1 Modulators | |
| | ACT-128800 | $S1P_1$ agonist |
| | SEW2871 | $S1P_1$ agonist |
| | GSK2018682 | $S1P_1$ agonist |
| | FTY720 | $S1P_1$ agonist |
| | ACT-128800 | $S1P_1$ agonist |
| | KRP203 | $S1P_1$ agonist |
| | FTY720 | $S1P_1$ agonist |
| | KRP203 | $S1P_1$ agonist |
| | MRS 2690 | adenosine $A_{2B}$ receptor agonist |
| | Dopamine | MSCs expressed the six subtypes of dopamine receptor and, correlating with this, dopamine addition increased basal migration, with a more pronounced effect in PB-MPCs |
| C | Catecholamines (Epinephrine, Norepinephrine etc.) | |
| | Dopamine, Epinephrine, norepinephrine and their downstream receptors (G proteins, adenylate cyclase, or alternatively PI3K/AKT) | |
| | L-Phenylalanine | Catecholamine precursors |
| | L-Tyrosine | Catecholamine precursors |
| | L-DOPA | Catecholamine precursors |
| | Dopamine | Catecholamine precursors |
| | Aripiprazole | Dopamine agonists |
| | Phencyclidine | |
| | Quinpirole | |
| | Salvinorin A | |
| | Apomorphine | |
| | Bromocriptine (Parlodel) | |
| | Cabergoline (Dostinex) | |

TABLE 1-continued

Cell mobilizing candidates.

| GROUP | Agent | Mechanism |
|---|---|---|
| | Ciladopa | |
| | Dihydrexidine | |
| | Dinapsoline | |
| | Doxanthrine | |
| | Epicriptine | |
| | Lisuride | |
| | Pergolide | |
| | Piribedil (Pronoran and Trivastal) | |
| | Pramipexole (Mirapex and Sifrol) | |
| | Propylnorapomorphine | |
| | Quinagolide (Norprolac) | |
| | Ropinirole | |
| | Rotigotine | |
| | Roxindole | |
| | Sumanirole | |
| | Fenoldopam selective for dopamine receptor D1 Cocaine, amphetamines, | |
| | acepromazine | Dopamine antagonists |
| | amisulpride | |
| | amoxapine | |
| | asenapine | |
| | azaperone | |
| | benperidol | |
| | bromopride | |
| | butaclamol | |
| | clomipramine (mild) | |
| | chlorpromazine | |
| | chlorprothixene | |
| | clopenthixol | |
| | domperidone | |
| | droperidol | |
| | eticlopride | |
| | flupenthixol | |
| | fluphenazine | |
| | fluspirilene | |
| | haloperidol | |
| | hydroxyzine | |
| | iodobenzamide | |
| | levomepromazine | |
| | loxapine | |
| | mesoridazine | |
| | metoclopramide | |
| | nafadotride | |
| | nemonapride | |
| | olanzapine | |
| | paliperidone | |
| | penfluridol | |
| | perazine | |
| | perphenazine | |
| | pimozide | |
| | prochlorperazine | |
| | promazine | |
| | quetiapine | |
| | raclopride | |
| | remoxipride | |
| | risperidone | |
| | spiperone | |
| | spiroxatrine | |
| | stepholidine | |
| | sulpiride | |
| | sultopride | |
| | tetrahydropalmatine | |
| | thiethylperazine | |
| | thioridazine | |
| | thiothixene | |
| | tiapride | |
| | trifluoperazine | |
| | trifluperidol | |
| | triflupromazine | |
| | ziprasidone, haloperidol, paliperidone, clozapine, risperidone, olanzapine, quetiapine, ziprasidone, metoclopramide, droperidol, domperidone, amoxapine, clomipramine, trimipramine, melatonin, Chonline | |

TABLE 1-continued

Cell mobilizing candidates.

| GROUP | Agent | Mechanism |
|---|---|---|
| | Bupropion Altropane (O-587) | Dopamine reuptake inhibitor |
| | Amfonelic acid (WEST 25978) | |
| | Amineptine (has a reasonable degree of selectivity for dopamine over norepinephrine reuptake inhibition) | |
| | BTCP (GK-13) | |
| | 3C-PEP (extremely potent and selective for dopamine transporter) | |
| | DBL-583 | |
| | Difluoropine (O-620) | |
| | GBR-12783 | |
| | GBR-12935 | |
| | GBR-13069 | |
| | GBR-13098 | |
| | GYKI-52895 | |
| | Iometopane ($\beta$-CIT, RTI-55) | |
| | Methylphenidate | |
| | Ethyphenidate | |
| | Modafinil | |
| | Armodafinil | |
| | RTI-229 | |
| | Vanoxerine (GBR-12909) | |
| | Haloperidol | |
| | Chlorpromazine | |
| | Eticlopride | |
| | Pimozide | |
| | Chlorpromazine | |
| | Eticlopride | |
| | Inhibitors of the catechol-O-methyltransferases (COMT) or deamination by monoamine oxidases (MAO) enzymes | Catecholamine degradation inhibitors |
| | Adenylate cyclase or their alternative phosphoinositide 3-kinase (PI3K)/Akt pathways. | Modulators of downstream cascade of Catecholamine receptors |
| | Agonists of Catecholamine receptors a1, a2, b1, b2 and b3 receptors, in certain instances blockers of the same | Propranolol, Isoproterenol have been shown to mobilize Epithelial stem cells (EPC) |
| | Desipramine and other drugs which inhibit reuptake of NE | a NE reuptake inhibitor, increases mobilization |
| | DRD1, DRD2, DRD3, DRD4, DRD4 receptor agonists and antagonists such as eticlopride | modulation of DRD2 receptor activity of MSCs |
| | Nicotine | increases Epinephrine, Norepinephrine, dopamine |
| | Clenbuterol | b2-adrenergic agonist, increases HSC mobilization |
| | Lidocaine and axonal inhibitor Family | Mechanism though the neuronal inhibition of the sympathetic/parasympathetic control of the nervous system. |
| D | Integrins receptor and ligands and modulators Alpha 4 and 9 integrin antagonists including antibodies to $\alpha_9\beta_1$ and $\alpha_4\beta_1$ | |
| | BOP; N-(Benzene-sulfonyl)- L-prolyl-L-O-(1-Pyrrolidinylcarbonyl)tyrosine) | integrin antagonist targets both alpha9beta1 and alpha4beta1 integrins Alpha4beta1 is ubiquitously expressed on all hematopoietic cells but the expression of alpha9beta1 is restricted to HSC/progenitors |
| | trans-4-[1-[[2-(5-Fluoro-2-methylphenylamino)-7-fluoro-6-benzoxazolyl]acetyl]-(5S)-[methoxy(methyl)amino]methyl-(2S)-pyrrolidinylmethoxy]cyclohexanecarboxylic acid | VLA-4 antagonist |
| | Natalizumab, | VLA-4 antagonist |
| | BIO5192 | VLA-4 antagonist |
| | Firategrast; UNII-OJY3SK9H5F | VLA-4 antagonist |
| | Bio-1211 | $\alpha 4\beta 1$ (VLA-4) |
| | IVL-745 | $\alpha 4\beta 1$ (VLA-4) |
| | TBC-4746 | $\alpha 4\beta 1$ (VLA-4) |
| | DW-908e | $\alpha 4\beta 1$ (VLA-4) |

TABLE 1-continued

Cell mobilizing candidates.

| GROUP | Agent | Mechanism |
|---|---|---|
| | R-411/Valetegrast | both α4β1 and α4β7 |
| | AJM-300 | both α4β1 and α4β7 |
| | SB-683699/Firategrast | both α4β1 and α4β7 |
| | CDP323 | both α4β1 and α4β7 |
| | Compound 14e | both α4β1 and α4β7 |
| E | MISC reported mobilizers | |
| | matrix metalloproteinases and their inducers such as Me6TREN | MMP-2 and MMP-9, Degrade and deactivate CXCL12 (SDF-1) induction of MMP9 expression via phosphoinositide-3 kinase and p38 mitogen-activated protein kinase pathway signaling |
| | dimethyloxallyl glycine (DMOG) | prolyl hydroxylase inhibitor |
| | GRObeta chemokine | |
| | sulfated colominic acid. | |
| | Beta-Chemokine CCL15 | Affects the adhesion and migration of hematopoietic progenitor cells. |
| | *panax notoginseng* saponins | |
| | VEGF | |
| | ALT-1188 | Demonstrating superior mobilization in mice than AMD3100 |
| | MRS2690 | P2RY14 agonist |
| | UDP-glucose | |
| | gamma-tocotrienol: | |
| | Me6TREN | |
| | TGF β | |
| | TGF-β1 | |
| | Substance P | |
| F | Indirect Actions via various cells Modulation of cells that produce cytokines that enable stem cell mobilization such as osteoblasts, endothelial cells | |

Different types of stem cells are needed in different types of applications. Mesenchymal stem cells are desired for regenerative medicine purposes. Hematopoietic stem cells are desired for bone marrow transplant uses. Epithelial stem cells are desired for vascular regenerative purposes. In certain embodiments, the solution comprises a composition selected for the extraction of a specific cell type, such as a stem cell or a stromal cell. This has been shown to be possible by selective activation of one or more types of receptors, including activation/inhibition of the dopamine DRD2 receptor. In certain embodiments, the solution comprises a composition selected for the extraction of a specific stem cell type, such as a hematopoietic stem cell, an endothelial stem cell, and a mesenchymal stem cell. For example, dopamine has been shown to be capable of increasing hematopoietic stem cell mobilization while inhibiting mesenchymal stem cell mobilization. In certain embodiments, the chemicals can be administered in various orders. For example, a chemical designed to mobilize stem cells from its native niche (via modulation of CXCR4, CXCL12, an integrin inhibitor or G-CSF, followed by a protease or protease inducer that acts generally on the binding of cells to the extracellular matrix, followed by an agent that acts via the nervous system, nerves, or the neural receptors.

As described elsewhere herein, the administered solution can decrease pain. The solution can include any suitable composition that can reduce the sensation of pain or mobilize stem cells. Non-limiting examples include one or more of lidocaine, prilocaine, tetracaine, benzocaine, procaine, mepivacaine, bupivacaine, etidocaine, tropacocaine, piperocaine, stovaine, cyclomethycaine, parethoxycaine, dyclonine, falicain, pramoxine, amolanone, phenacene, deprodone, dibucaine, and the like.

The various compositions described herein may be present as salts even if salts are not depicted and it is understood that the invention encompasses all salts and solvates of the compositions depicted, as well as non-salt and non-solvate forms, as is well understood by persons skilled in the art. The various compositions described herein also encompass stereochemical forms, including any enantiomeric or diasteriomeric forms of the compositions depicted. The recitation of a structure or name herein is intended to include all possible stereoisomers of the compositions depicted, such as crystalline or non-crystalline forms. Compositions can also include substantially pure compositions, including a specific stereochemical form thereof, or a composition comprising stereochemical mixtures in any ratio. The various compositions described herein also encompass analogs and derivatives having a structure similar to the depicted compositions but differing with respect to certain components or structural makeup, such as linking atoms or groups with longer or shorter linkers, or ring groups with different number of atoms.

The solutions of the invention can be formulated using one or more pharmaceutically acceptable excipients or carriers. Pharmaceutically acceptable carriers that are useful, include, but are not limited to, glycerol, water, saline, ethanol and other pharmaceutically acceptable salt solutions such as phosphates and salts of organic acids. Additional ingredients can include, but are not limited to, one or more of the following: excipients; dispersing agents; inert diluents; binding agents; lubricating agents; preservatives; suspending agents; dispersing agents; buffers; antioxidants; antibiotics; antifungal agents; stabilizing agents; and the like.

In some embodiments, the methods of the present invention are also capable of harvesting trabecular bone. For example, as the aspiration device is advanced into position, it cuts bone pieces at its distal end, which have rake and relief angles shown experimentally to be ideal for cutting bone with the least force and least heat generation. These bone pieces are channeled via flutes into the lateral openings of the device, which rake these pieces into the device lumens for harvesting. This has important implications in regenerative medicine therapies, as both bone and bone marrow are often needed to aid in spinal fusions and other orthopedic procedures. Sometimes the bone marrow is so packed with cells that no liquid marrow can be obtained—so called "dry tap". The method of obtaining trabecular bone for analysis is thereby useful even when no marrow can be obtained. Cells are "disaggregated" as the device macerates the bone while advancing into aspiration position, rendering the cells harvestable.

In some embodiments, the methods of the present invention are also capable of inducing a flushing action to facilitate displacement of matter from a target site. For example, the devices and methods can be used to wash away calcium deposits in calcific tendonitis and tumoral calcinosis or to non-invasively flush out a joint for hemarthrosis or infection.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Intraosseous Method for Pharmacologic Mobilization of Stem Cells

In a typical bone marrow aspiration (BMA) procedure, when stem cells near an aspiration port are harvested, venous blood inevitably flows in from the sinusoids, contaminating the sample and limiting the stem cells harvested. A slow infusion of a drug into the bone is able to diffuse throughout nearly the entire bone because it is a large interconnected venous space, much like a sponge. Too fast of an infusion merely pushes the drug into the venous system rather than the bone. By first pharmacologically flooding venous spaces of the bone, stem cells remote from the site of aspiration can be harvested with the sinusoidal blood, greatly improving yields beyond the reaches of existing device configurations. Subcutaneous and IV pharmacological methods are too protracted to be useful for the intra-procedural harvesting needed for regenerative medicine and cancer diagnosis. Intraosseous infusion ensures peak concentrations directly in the bone marrow that will rapidly mobilize the stem cells which can be directly aspirated. Preliminary data using the common and inexpensive drug lidocaine surprisingly and unexpectedly led to significantly increased yields compared to controls by more than 200% (FIG. 27A, FIG. 27B), demonstrating that lidocaine has a mobilizing effect. The unique dual-lumen configuration of the novel BMA device enables the delivery of a drug at a site remote from the aspiration, allowing drug diffusion to the site of aspiration without washing away the stem cells to be aspirated. Moreover, lidocaine is effective in whole-bone anesthesia, which allows for painless aspiration (Manohar M et al., Veterinary Radiology & Ultrasound 17.4 (1976): 152-156; Tobias J D et al., Pediatric emergency care 6.2 (1990): 108-109; Waisman M et al., Journal of Trauma and Acute Care Surgery 39.6 (1995): 1153-1156; Replogle K et al., The Journal of the American Dental Association 130.5 (1999): 649-657; Chamberlain T M et al., General dentistry 48.3 (1999): 299-302; Joseph G et al., Journal of clinical anesthesia 20.6 (2008): 469-473; Ngo A S Y et al., International journal of emergency medicine 2.3 (2009): 155-160; Philbeck T E et al., JEMS: a journal of emergency medical services 35.9 (2010): 58-62; Tobias J D et al., Anesthesia & Analgesia 110.2 (2010): 391-401; Sokov E L et al., Terapevticheskii arkhiv 85.4 (2012): 61-65). However, when lidocaine infusion was performed with a conventional device, the yields were significantly lower than the control, indicating that the stem cells at the site of infusion were being washed away by the infusion with the configuration of the conventional device.

Figure 27A:
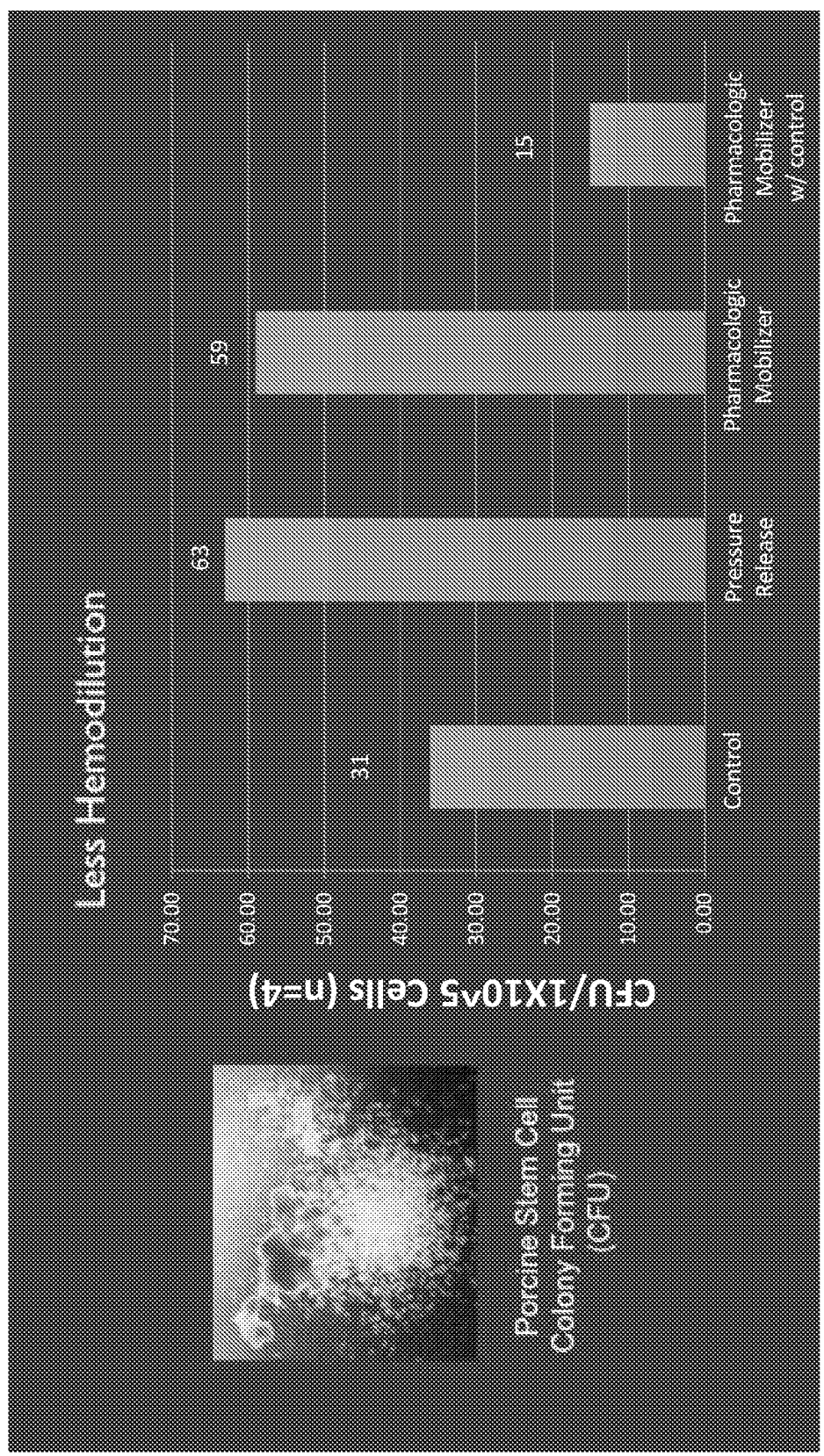
FIG. 27A and FIG. 27B depict the results of experiments comparing aspiration performance using a control method, using the aspiration device of the present invention, using the aspiration device of the present invention with a pharmacologic mobilizer, and using a control method with a pharmacologic mobilizer.
Figure 27B:
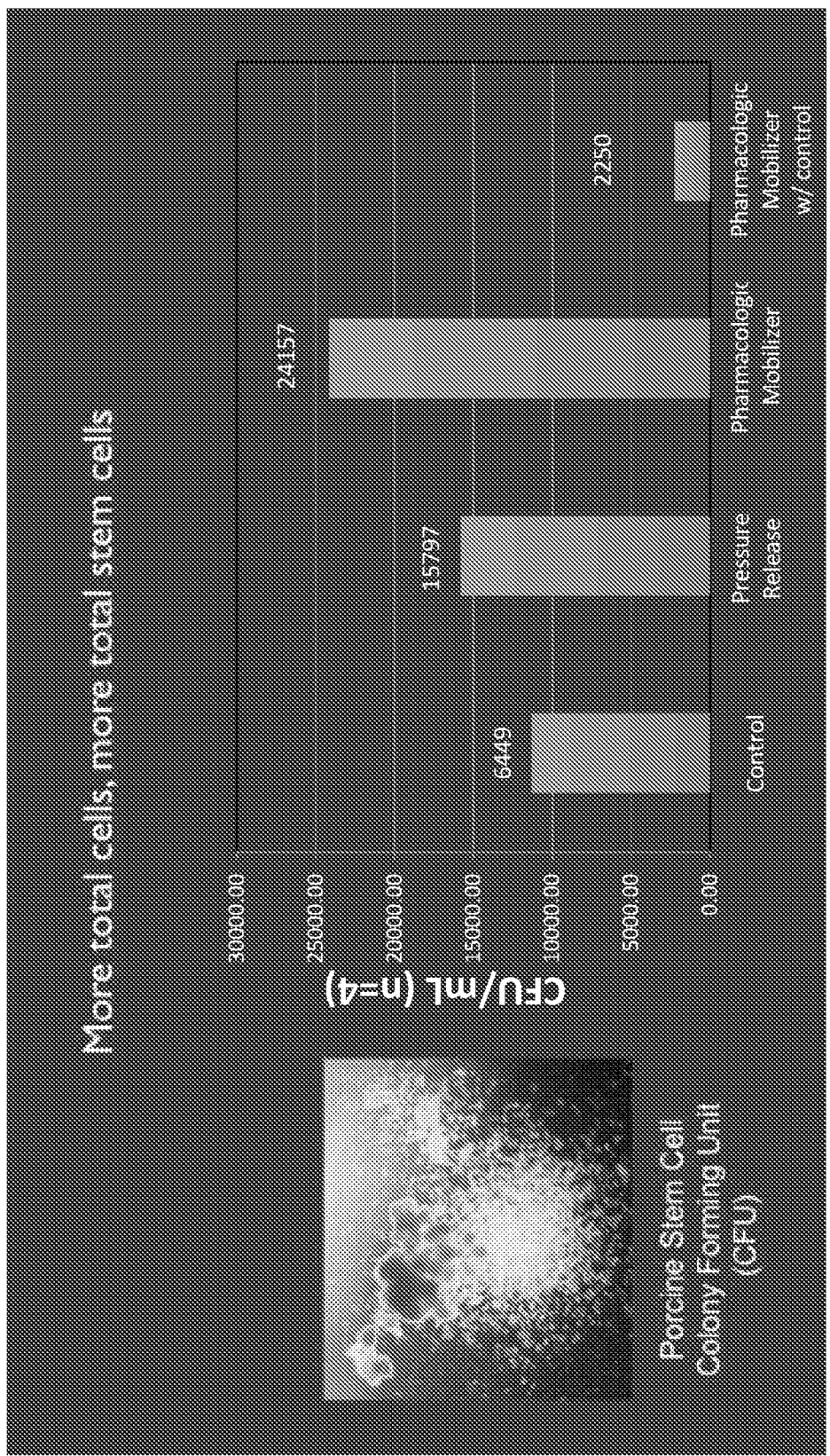

The colony forming unit (CFU) assay is an accepted measure of relative stem cell concentrations in BMA. Stem cells develop into colonies whereas mature cells do not. A preliminary (N=4) trial of BMA in a live porcine model was performed comparing a single-hole cancer aspiration device to the novel dual-lumen BMA method. The novel dual-lumen device with pressure modulation provided more CFU/mL than the control. The novel dual-lumen device with lidocaine infusion (without the pressure modulation) more than doubled the CFU/mL (FIG. 27A).

Example 2: Resolving Sampling Errors

In cancer diagnoses, there are three main sources of sample errors. The first source is the "dry tap," where no marrow can be obtained (6.8% of aspirates). While this can be seen in normal patients, it can represent significant disease, such as when the marrow is so tightly packed with tumor cells that no liquid marrow can be obtained. It can also occur after chemotherapy, when all stem cells in the marrow have been ablated, as well as in fibrotic marrow such as in the condition myelofibrosis. The second source is from aspicular samples (20.6% of aspirates). This is a result of a small sampling area combined with the random distribution of spicule-containing hematopoietic marrow throughout the bone. It happens when the sampling needle is positioned in an area containing fatty marrow rather than the red hematopoietic marrow. This marrow distribution is readily visible on MRI but it would be very burdensome to guide each aspiration with MRI.

The third source is from hemodilution (27% of aspirates), where numerous tiny venous sinusoids drain into a bone cavity and it can be considered a large venous space. The venous space is sometimes even mistaken for a vein in an emergency setting. This collection of blood flows is drawn to an aspiration vacuum. Early investigators have demonstrated that dilution of the bone marrow aspirate with peripheral blood and the mature cells is inevitable during bone marrow aspiration. In another study in patients with hematologic disease, 6-93% of the nucleated cells were derived from the blood, the greatest admixture occurring in patients with leukemia. If more than 2 mL is aspirated, more marrow is not aspirated as would be expected; rather, venous blood flows into the needle preferentially to the bone marrow due to a much lower resistance to flow from these venous channels. Multiple studies have demonstrated that only 1-2 mL of marrow can reliably be obtained from a single position, and that a larger aspirated volume from a single position lowers the yield. In another study, the first 1.0 mL of marrow aspirated from healthy donors was found to be 8% contaminated with peripheral blood mononuclear cells (PBNC), while subsequent aspirates performed for marrow harvesting were 20% contaminated with nucleated blood cells.

In experiments with 51Cr-labelled autologous red cells and 125I-labeled albumin, approximately 97% of the hemoglobin in the bone marrow aspirate is derived from the peripheral blood, whether at the beginning or the end of an aspiration, suggesting that bone marrow cells are aspirated within the blood fluid volume. Importantly, up to 10-20 mL of sample can be required for analysis depending on the number of tests needed, with the higher amount needed if the patient is in a clinical trial, which may require more marrow.

While this hemodilution is technique and patient dependent, it remains a significant limitation despite optimized checklists and despite CT guidance. In particular it confounds the ratio of mature to immature cells. The peripheral/venous blood of the marrow contains mature cells, whereas the marrow contains both the stem cells (immature) and the mature cells. The ratio of these cells is the gold standard for classification of Myelodysplastic syndrome (MDS) and Acute Myelogenous Leukemia (AML) and therefore dilution of this ratio by peripheral blood is a major factor in reducing sensitivity in MDS and AML diagnosis.

In leukemia, blast counts are used in diagnosis and prognostication/risk stratification and also as diagnostic criteria for recurrent and residual disease. Hemodilution has been shown to have an adverse effect on risk stratification in children with acute lymphoblastic leukemia. In a study evaluating minimal residual disease in treated acute myelogenous leukemia, blast percentage changed 83% in the hemodilute specimens compared to the non-hemodilute specimens, and 4/9 (44%) of the subjects were upgraded to the 0.1% cut off for the "minimal residual disease" using the non-hemodilute samples. Contamination with peripheral blood is important not only in search for MRD, but also at the time of diagnosis, in cases where 25% of blasts are in the bone marrow and 0% in the peripheral blood; a dilute sample may show less than the 25% of the blasts, yielding an incorrect diagnosis.

In myelodysplastic syndrome (MDS), blast thresholds ascend in arbitrary discrete steps of 5%, 10%, and 20%, and the likelihood of a change in category would depend on the proximity of blast counts to threshold values, as well as upon the degree of peripheral blood dilution of the sample. In one study involving 66 patients with MDS, attempts to control for hemodilution resulted in re-classification of the disease in an astonishing 33% of patients. In another study, dilution of peripheral blood significantly limited flow cytometry in classifying disease in MDS, with up to 26.8% of patients reclassified when correction for hemodilution. This correction could only be applied with the bone marrow purity was above 40%.

In another effort to quantify the effect of hemodilution, a retrospective review was performed on bone marrow aspiration and biopsy results from 355 patients with MDS that had at least one bad aspirate. The hemodilute aspirate was compared to subsequent or repeat aspirates to estimate the clinical significance of the hemodilute aspirations. Of the 1250 aspirates, 470 (37%) were limited and 58% of these were felt to be clinically significant (22% of all aspirates in MDS), 4% had a missed major diagnosis, 7.7% required a re-biopsy, and 46% were felt to be clinically significant due to a decreased level of confidence in the blast count or an inability to assess for dysplasia.

Previous Attempts to Overcome Sampling Errors

Dry taps: many authors have suggested that roll imprints be performed in the setting of a dry tap. This is when a core trephine biopsy is rolled onto a slide to simulate a bone marrow smear. However, these are very technique dependent with an effectiveness ranging from as low as 10% to 60%. Another alternative method for compensating for dry taps is called "disaggregation," where an additional core biopsy is performed and the entire volume of cells within that biopsy are isolated from the bone by either mechanical or enzymatic means, which not only allow for a surrogate of a bone marrow smear but also cytogenetics and flow cytometry. A 2005 study demonstrated 60% of samples yielded a good-quality aspirate-like analysis with an additional 13% (total 75%) yielding a moderate but still informative quality. However, this requires the patient to have an additional or longer biopsy and therefore is not routine in clinical practice.

Aspicular samples: optimized technique using training and checklist interventions sought to overcome the problem of aspicular samples. In a prospective 2013 study, 18.5% of samples were aspicular prior to the intervention and 20% after the intervention and aspicular samples had a non-diagnostic rate of 20%. Anecdotal beliefs of hematologists suggest that needle positioning may be a cause of aspicular samples; however the use of CT scan and perfect positioning in the iliac crest did not improve the rate of aspicular samples in a subset analysis of the retrospective review of sample quality.

Hemodilution: attempts to overcome this long-time bane of bone marrow aspirations dates back to the 1960s with the addition of side holes at the tip of the needle. This is still thought by many to increase the surface area of aspiration and therefore increase yields of marrow over blood. However, because a substance naturally flows to the site of least resistance, blood will still preferentially flow through the large end-holes in these devices or a side hole that may be connected to the venous lakes within a marrow cavity. A randomized study showed that these side holes do not increase a marrow yield which was substantiated by a 2011 study. Some data suggests increasing needle core diameter increases yields. However, no device adequately addresses the main issue: a device with an open end hole can only aspirate 1-2 mL from a single position in the bone without causing hemodilution. Such a device must be repositioned to a different location in the bone requiring additional pain and discomfort for the patient and therefore it is not feasible in clinical practice. As no current device adequately addresses the issue of hemodilution, pathologists have tried to compensate after the fact using a variety of tactics. This includes performing cell counts on a smaller number of cells, though it is not the standard of care and merely attempts to control for the dilutive affect using flow cytometry of both venous blood and marrow concomitantly, which is partially effective but only if the marrow sample is "pure enough" (40-90% pure). It has been suggested by lead researchers that these methods are not practical or not applicable in most situations.

Innovations to Overcome Sampling Errors

Dry taps: as stated above, "disaggregation" of cells from the trephine bone is a very effective means of obtaining an aspirate-like analysis in the setting of a dry tap, but is not used in clinical practice because there is no streamlined way to send the sample and it requires an additional biopsy for the patient. Current needles compress the marrow tissue away from the needle as the needle is advanced through bone into the aspirate position. The aspiration device of the present invention is designed to mince bone via serrations as it is advanced into aspirate position. The serrations have rake and relief angles shown to be ideal for cutting through bone tissue with the least force and the least heat generation. These pieces will be harvested into a large aspiration chamber which itself has a short rake angle and can either be aspirated with the aspirate samples or removed with the stylet that has a ledge-like catchment that brings all solid pieces from the device as the stylet is removed (see FIG. 16 through FIG. 18). These solid pieces can be placed in a relatively inexpensive machine for cell disaggregation and subsequent aspirate-like analysis.

Aspicular samples: as discussed, aspicular samples are thought to be due to the positioning of the aspirate needle in fatty marrow rather than hematopoietic marrow. There is a random distribution of hematopoietic marrow within the bone marrow, which may be sparsely scattered in many patients. This is one reason why the World Health Organization (WHO) requires a bone core biopsy to be 2 cm in length for adequate diagnosis. To decrease this sampling artifact, the length of sampling within the bone and total volume of bone that is sampled must be increased to be equal to that of the bone core biopsies. Increasing the length across which the bone is sampled will increase the probability that the needle will cross an island of hematopoietic marrow during aspiration to harvest the spicules. This increased sampling length can be accomplished in the devices of the present invention by aspirating through a single elongated side-hole that measures 10 mm combined with occlusion of the end hole during aspiration by the stylet that remains in place. The aspiration thereby occurs around the stylet (See FIG. 10B). Other needles exist with side holes but the end hole, being the largest hole, will always be the dominant aperture in the aspiration. Moreover, other needles with side holes scatter them around the circumference of the needle and therefore the user is uncertain as to which hole actually harvested marrow, whereas the use of a single hole allows the user to control the rotational angle at which the hole faces. By occluding the end hole during aspiration, the aspiration occurs across a defined length of a side hole rather than at the end point. Retention of the stylet allows the needle to be moved in or out of the bone during or in between separate aspirations. This allows the aspiration to occur across a length of bone equivalent to that required by the WHO for bone cores.

Increasing the area of sampling is accomplished not only by an elongated hole, but a user can also rotate the needle and compound this increased surface area circumferentially about the needle. Occluding the end hole with stylet retention during aspiration allows exclusive aspiration from the side hole; therefore the user can control the area of aspiration of the bone by controlling the rotational angle that the aspirate chamber faces within the bone. Thus a, an exemplary 10 mm side hole can be rotated 6 times for a circumferential aspiration at each 10 mm depth location. Considering 2 depths within the same aspiration site accounts for a 48 fold increase in sampled area.

Hemodilution: The main issue with hemodilution is that only 1-2 mL can be aspirated from any given location of the marrow before contamination with peripheral blood with current methods that do not modulate negative pressure. The clinical need is to be able to aspirate from multiple distinct areas within the bone marrow cavity, within a single bone entry site. This is also accomplished, for example, by the exclusive aspiration from a single side hole, occlusion of the end hole, and the user controlling the rotational angle of the direction the aspiration hole faces. For example, 6 rotational locations at 2 different depths allows for 12 or more distinct aspiration locations. By limiting aspiration to 1-2 mL per location, up to 24 mL of "pure marrow" can be obtained.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An intraosseous method for delivering a pharmacologic composition to mobilize and collect a concentration of stem cells, the method comprising:
    inserting an aspiration device into a bone marrow tissue; wherein the aspiration device has at least one elongate member with a lumen extending between a proximal opening and a distal opening;
    administering a stem cell mobilizing composition through the distal opening of the at least one elongate member into a first location of the bone marrow tissue;
    diffusing the administered stem cell mobilizing composition into a second location of the bone marrow tissue that is remote from the first location of the bone marrow tissue, thereby mobilizing the stem cells in the bone marrow tissue such that the stem cells have an increased concentration at the second location of the bone marrow tissue as compared to prior to the administration of the stem cell mobilizing composition; and
    collecting, after a delay of between 30 seconds and 120 minutes from the administration of the stem cell mobilizing composition, a bone marrow tissue sample at the second location of the bone marrow tissue containing the stem cells, wherein a number of stem cells collected is at least 50% greater than compared to a theoretical number of stem cells collected without the administration of the stem cell mobilizing composition into the first location of the bone marrow tissue.

2. The method of claim 1, wherein the collected bone marrow tissue sample is further processed in a biopsy analysis, an aspiration procedure, or a cell harvest procedure.

3. The method of claim 2, wherein the biopsy analysis is a cancer biopsy analysis for Myelodysplastic syndrome (MDS) or Acute Myelogenous Leukemia (AML).

4. The method of claim 1, wherein the stem cell mobilizing composition comprises an agent that acts by one or more of the following: mobilizing the stem cells from their native milieu; blocking inhibition of the stem cells' departure; decreasing adhesion of the stem cells to their surrounding environment; modulating neural or cellular control that dictate stability, ingress, or egress of the stem cells from their milieu; modulating a molecule within a molecular pathway involved with the adhesion or the mobilization of the stem cells; activating or inhibiting dopamine DRD2 receptor; acting on binding of the stem cells to an extracellular matrix; and acting via a nervous system, nerves, or neural receptors.

5. The method of claim 4, wherein the stem cell mobilizing composition is selected from the group consisting of: a modulator of an integrin family, VLA-4 molecule inhibitors firategast, UNII-OJY3SK9H5F, BI05192, a modulator of CXCL12/CXCR4 interaction, AMD3100, a modulator of CXCR7 molecule, CXCL12 analogues, a modulator of nerve/stem cell interaction, a modulator of dopamine, a modulator or inhibitor of nerve axon firing, a modulator of an adhesion molecule, integrins, G-protein coupled receptors, SIP-1 agonists, endocrine targets, plerixafor, granulocyte colony-stimulating factor (G-CSF), PEGylated and glycosylated versions of G-CSF, granulocyte macrophage colony-stimulating factor (GM-CSF), macrophage colony stimulating factor (M-CSF), tyrosine kinase 3 (FLT-3), ancestim, a stem cell factor, a cytokine, interleukin-1, interleukin-3, interleukin-6, interleukin-7, interleukin-11, interleukin-12, a metalloproteinase, a serine protease, a cysteine protease, a peptidase, a chemokine, a chemotherapeutic, a cyclophosphamide, dopamine, and combinations thereof.

6. The method of claim 4, wherein the method comprises sequential administration at the first location of the bone marrow tissue of a CXCR4 inhibitor, a VLA-4 or metalloproteinase or ISP-1 agonist, a compound that modulates neural-stem cell control, and a molecule that impairs the stem cell adhesion.

7. The method of claim 1, wherein the second location of the bone marrow tissue includes a surrounding extracellular milieu/matrix including a surrounding vascular space.

8. The method of claim 1, the method further comprising administering a pain reducing composition at the first location of the bone marrow tissue selected from the group consisting of: lidocaine, prilocaine, tetracaine, benzocaine, procaine, mepivacaine, bupivacaine, etidocaine, tropacocaine, piperocaine, stovaine, cyclomethycaine, parethoxycaine, dyclonine, falicain, pramoxine, amolanone, phenacene, deprodone, dibucaine, and combinations thereof.

9. The method of claim 1, wherein the aspiration device additionally comprises a pressure modulating mechanism that equalizes bone marrow vacuum pressure.

10. The method of claim 1, wherein the collected bone marrow tissue sample comprises one or more cells selected from the group consisting of: hematopoietic stem cells, mesenchymal stem cells, epithelial stem cells, stromal cells, gland cells, nerve cells, fat cells, germ cells, and combinations thereof.

11. The method of claim 10, wherein less than 10% of the one or more cells from the collected bone marrow tissue sample are blood cells.

12. The method of claim 1, wherein the number of stem cells collected is at least 200% greater than compared to the theoretical number of stem cells collected without the administration of the stem cell mobilizing composition into the first location of the bone marrow tissue.

13. An intraosseous method for delivering a pharmacologic composition to mobilize and collect a concentration of stem cells, the method comprising:
inserting an aspiration device into a bone marrow tissue, wherein the aspiration device has at least one elongate member with a lumen extending between a proximal opening and a distal opening;
administering a stem cell mobilizing composition through the distal opening of the at least one elongate member into a first location of the bone marrow tissue;
diffusing the administered stem cell mobilizing composition into a second location of the bone marrow tissue, the second location of the bone marrow tissue being proximal to the distal opening of the at least one elongate member and remote from the first location of the bone marrow tissue, thereby mobilizing the stem cells in the bone marrow tissue such that the stem cells have an increased concentration at the second location of the bone marrow tissue as compared to prior to the administration of the stem cell mobilizing composition; and
collecting a bone marrow tissue sample at the second location of the bone marrow tissue after a delay of between 30 seconds and 120 minutes from the administration of the stem cell mobilizing composition, wherein the collected bone marrow tissue sample contains at least a portion of the mobilized stem cells.

14. The method of claim 13, wherein a number of stem cells collected is at least 50% greater than compared to a theoretical number of stem cells collected without the administration of the stem cell mobilizing composition into the first location of the bone marrow tissue.

15. An intraosseous method for delivering a pharmacologic composition to mobilize and collect a concentration of stem cells, the method comprising:
inserting an aspiration device into a bone marrow tissue, wherein the aspiration device has an elongate member with a first lumen and a second lumen within the elongate member, and wherein the first lumen has a distal end opening at a distal end of the elongate member, and wherein the second lumen has a distal end opening that is separate and proximal to the distal end opening of the first lumen;
administering a stem cell mobilizing composition through the distal opening of the first or second lumen into a first location of the bone marrow tissue surrounding the distal opening of the first or second lumen from which the stem cell mobilizing composition was administered;
diffusing the administered stem cell mobilizing composition into a second location of the bone marrow tissue surrounding the distal opening of the first or second lumen not used for the administration of the stem cell mobilizing composition, wherein the second location of the bone marrow tissue is remote from the first location of the bone marrow tissue, thereby mobilizing the stem cells in the bone marrow tissue such that the stem cells have an increased concentration at the second location of the bone marrow tissue as compared to prior to the administration of the stem cell mobilizing composition; and
collecting, after a delay of between 30 seconds and 120 minutes from the administration of the stem cell mobilizing composition, a bone marrow tissue sample from the second location of the bone marrow tissue containing at least a portion of the mobilized stem cells, wherein the collection occurs through the distal opening of the first or second lumen not used for the administration of the stem cell mobilizing composition, and wherein a number of stem cells collected is at least 50% greater than compared to a theoretical number of stem cells collected without the administration of the stem cell mobilizing composition into the first location of the bone marrow tissue.

* * * * *